US007364726B2

(12) United States Patent
Hiserodt et al.

(10) Patent No.: US 7,364,726 B2
(45) Date of Patent: *Apr. 29, 2008

(54) PHARMACEUTICAL COMPOSITION FOR CANCER TREATMENT CONTAINING CELLS THAT EXPRESS A MEMBRANE CYTOKINE

(75) Inventors: John C. Hiserodt, Huntington Beach, CA (US); Martin R. Graf, Richmond, VA (US); Gale A. Granger, Laguna Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/875,349

(22) Filed: Jun. 5, 2001

(65) Prior Publication Data

US 2001/0038841 A1     Nov. 8, 2001

Related U.S. Application Data

(62) Division of application No. 08/901,225, filed on Jul. 24, 1997, now Pat. No. 6,277,368.

(60) Provisional application No. 60/029,286, filed on Oct. 29, 1996, provisional application No. 60/023,108, filed on Jul. 25, 1996.

(51) Int. Cl.
    *A61K 48/00* (2006.01)
(52) U.S. Cl. .................................. 424/93.2
(58) Field of Classification Search ............ 424/277.1, 424/184.1; 530/333
    See application file for complete search history.

(56) References Cited

U.S. PATENT DOCUMENTS

| | | | |
|---|---|---|---|
| 4,847,201 A | | 7/1989 | Kawasaki et al. |
| 5,109,113 A | | 4/1992 | Caras et al. |
| 5,290,551 A | | 3/1994 | Berd |
| 5,382,427 A | | 1/1995 | Plunkett et al. |
| 5,399,346 A | | 3/1995 | Anderson et al. |
| 5,484,596 A | | 1/1996 | Hanna, Jr. et al. |
| 5,637,483 A | * | 6/1997 | Dranoff et al. .......... 424/93.21 |
| 5,681,562 A | | 10/1997 | Sobol et al. |
| 5,759,535 A | | 6/1998 | Cohen et al. |
| 5,866,115 A | | 2/1999 | Kanz et al. |
| 5,891,432 A | | 4/1999 | Hoo |
| 6,051,218 A | | 4/2000 | McBride |
| 6,277,368 B1 | | 8/2001 | Hiserodt et al. |
| 2001/0036458 A1 | | 11/2001 | Hiserodt et al. |

FOREIGN PATENT DOCUMENTS

| | | |
|---|---|---|
| DE | 441425 | 10/1995 |
| EP | 538952 | 4/1993 |
| EP | 569678 | 11/1993 |
| WO | WO 92/05262 | 2/1992 |
| WO | WO 92/05805 | 4/1992 |
| WO | WO 93/07906 | 4/1993 |
| WO | WO 95/16775 | 6/1995 |
| WO | WO 95/23216 | 8/1995 |
| WO | WO 95/31107 | 11/1995 |
| WO | WO 96/05866 | 2/1996 |
| WO | WO 96/07433 | 3/1996 |
| WO | WO 96/29394 | 9/1996 |
| WO | WO 97/20938 | 6/1997 |
| WO | WO 97/28251 | 8/1997 |
| WO | WO 98/06746 | 2/1998 |
| WO | WO 98/16246 | 4/1998 |
| WO | WO 98/48012 | 10/1998 |
| WO | WO 99/06544 | 2/1999 |

OTHER PUBLICATIONS

Kimura et al (Exp Hematol Feb. 1996;24(2):360-3).*
Chen et al (Blood 2002; 100:1373-80).*
Jadus et al (Blood Jun. 15, 1996;87(12):5232-41).*
Tuck et al (Blood Oct. 1, 1994; 84(7):2182-8).*
Dermer (Bio/Technology Mar. 12, 1994; p. 320).*
Weiss (Washington Post May 6, 1998; A3).*
Dick JE et al (Cancer Surv. 1992;15:161-81.).*
Cosman et al (Behring. Inst. Mitt. Aug. 1998; (83):15-26).*
Asher et al (J. Immunol 1991; 146(9):3227-3234).*
Karp et al (J. Immunol 1992; 149(6):2076-2081).*
Abe et al., "Cytokine-gene-modified tumor vaccination intensified by a streptococcal preparation OK-432" *Cancer Immunol. Immunother.* (1995) 41:82-86.
Allione et al. "Immunizing and curative potential of replicating and nonreplacing murine mammary adenocarcinoma cells engineered with interleukin (IL-)2,IL-4,IL-6, IL-7, IL-10, tumor necrosis factor, granulocyte-macrophage colony-stimulating factor, and -interferon gene or admixed with conventional adjuvants" *Cancer Res.* (1994) 54:6022-6026.
Asher et al. "Murine tumor cells transduced with the gene for tumor necrosis factor-" *J. Immunology.* (1991) 146:3227-3234.
Berd et al. "Treatment of metastatic melanoma with an autologous tumor-cell vaccine: Clinical and immunologic results in 64 patents" *J. Clin. Oncol.* (1990) 8:1858-1867.

(Continued)

*Primary Examiner*—Christopher Yaen
(74) *Attorney, Agent, or Firm*—Carol L. Francis; Bozicevic, Field & Francis LLP

(57) ABSTRACT

This invention comprises cellular vaccines and methods of using them in cancer immunotherapy, particularly in humans. The vaccines comprise a source of tumor-associated antigen, and a cytokine-secreting cell line. Tumor antigen may be provided in the form of primary tumor cells, tumor cell lines or tumor extracts prepared from the subject. In certain embodiments of the invention, the cytokine-secreting line is a separate tumor line that is allogeneic to the patient and genetically altered so as to produce a cytokine at an elevated level. Exemplary cytokines are IL-4, GM-CSF, IL-2, TNF-α, and M-CSF in the secreted or membrane-bound form. In these embodiments, the cytokine-producing cells provide immunostimulation in trans to generate a specific immune response against the tumor antigen. Vaccines may be tailored for each type of cancer or for each subject by mixing tumor antigen with a favorable number of cytokine-producing cells, or with a cocktail of such cells producing a plurality of cytokines at a favorable ratio.

58 Claims, 8 Drawing Sheets

OTHER PUBLICATIONS

Blankenstein et al. "Tumor suppression after tumor cell-targeted necrosis factor gene transfer" *J. Exp. Med.* (1991) 173:1047-1052.

Borden, Ernst C. and Sondel, Paul M., "Lympokines and Cytokines as Cancer". 65:800-814, (1990).

Borrelli, Emiliana, et al. "Targeting of an Inducible Toxic Phenotype in Animal Cells." *Proc. Natl. Acad. Sci. USA.* 85:7572-7576 (1988).

Brown, D. "Gene Therapy 'Oversold' by Researchers, Journalists,"The Washington Post, A22, Dec. 8, 1995.

Bubenik, J. et al., "Immunotherapy of Cancer using Local Administration of Lymphoid Cells Transformed by IL-2c DNA and Constitutively Producing IL-2". *Immunology Letters* 23:287-292 (1998/1990).

Bubenik, J. et al., "Local Administration of Cells Containing an Inserted IL-2 Gene and Producing U2 Inhibits Growth of Human Tumors in Nu/Nu Mice." *Immunology Letters.* 19:279-282 (1988).

Coghlan, A. "Gene dream fades away,"New Scientist, vol. 145:14-15, Nov. 25, 1995.

Colombo, "Tumor cells engineered to produce cytokines or cofactors as cellular vaccines: do animal studies really support clinical trials?" *Cancer Immunol. Immunother.* (1995) 41:265-270.

Colombo, et al. "Granulocyte Colony-stimulating a Factor Gene Transfer Suppresses Tumorigenicity of a Murine Adenocarcinoma in Vivo." *J. Exp. Med.* 173:889-897 (1991).

Dillman et al., "Establishing in vitro cultures of autologous tumor cells for use in active specific immunotherapy" *J. Immunother.* (1993) 14:65-69.

Dranoff et al., "Vaccination with irradiated tumor cells engineered to secrete murine granulocytemacrophage colony-stimulating factor stimulates potent, specific, and long lasting anti-tumor immunity" *Proc. Natl. Acad. Sci. USA* (1993) 90:3539-3543.

Fakhrai et al., "Cytokine gene therapy with interleukin-2 transduced fibroblasts: effects of IL-2 dose on anti-tumor immunity" *Human Gene Therapy* (1995) 6:591-601.

Fearon et al., "Interleukin-2 production by tumor cells bypasses T helper function in the generation of an antitumor response" *Cell* (1990) 60:397-403.

Gabrilove, Janice l.and Jakubowski, Ann "Hematopoetic Growth Factors: Biology and Clinical Application". *J of the National Cancer Inst. Monographs.* 10:73-77 (1990).

Gandolfi, L. et al., "Intratumoral Echo-guided Injection of Interleukin-2 and Lymphokine Activated Killer Cells in Hepatorcellular Carcinom." *Hepato-gastroenterol* 36:352-356 (1989).

Gansbacher Bernd, et al., "Retroviral Vector-Mediated. Tau. Interferon Gene Transfer into Tumor Cells Generates Potent and Anti-tumor Immunity." *Cancer Research* 50:7820-7825 (1990).

Gansbacher, Bernd et al., "Interleukin 2 Gene Transfer into Tumor Cells Abrogates Tumorigenicity and Induces Protective Immunity", *J. Exp. Med*, 90:1237-1224 (1990).

Gansbacher, et al. "Retroviral Vector-Mediated Cytokine-Gene Transfer into Tumor Cells." *Cancer Investigation*, vol. 11(3):345-354, Mar. 1993.

Golumbek et al., "Controlled release, biodegradable cytokine depots: a new approach in cancer vaccine design" *Cancer Research* (1993) 53:5841-5844.

Golumbek et al., "Herpes simplex-1 virus thymidine kinase gene is unable to completely eliminate live, nonimmunogenic tumor cell vaccines" *J. Immunother.* (1992) 12:224-230.

Golumbek et al., "Treatment of established renal cancer by tumor cells engineered to secrete interleukin-4" *Science* (1991) 254:713-716.

Graf et al. Development of systemic immunity to glioblastoma multiforme using tumor cells genetically engineered to express the membrane-associated isoform of macrophage colony-stimulating factor. *J. Immunol.* 163:5544, 1999.

Graf et al., "Adenovirus-mediated gene transfer into experimental rat gliomas" *Soc. Neuroscience* (1995) 21:2135 (Abstract 838.5).

Graf et al., "T9 rat glioma cells secreting human TNF immunize Fischer rats against untransfected T9 and L9 gliomas" *Proc. Amer. Assoc. Cancer Res.* (1994) 35:500 (Abstract 2978).

Hoover, H.C. Jr. et al., "Delayed Cutaneous Hypersensitivity to Autologous Tumor Cells in Colorectal Cancer Patients Immunized With the Autologous Tumor Cell": *Bacillus-calmette guerin* Vaccine, *Cancer Res.* 44:1671-1676 (1984).

Jadus et al. Macrophages can recognize and kill tumor cells bearing the membrane isoform of macrophage colony stimulating factor. *Blood* 87:5232, 1996.

Jaffee et al. Considerations for the clinical development of cytokine gene-transduced tumor cell vaccines. *Methods* 12:143, 1997.

Karp et al. In vivo activity of tumor necrosis factor (TNF) mutants. Secretory but not membrane-bound TNF mediates the regression of retrovirally transduced murine tumor. *J. Immunol.* 149:2076, 1992.

Karp et al., "Cytokine secretion by genetically modified nonimmunogenic murine fibrosarcoma" *J. Immunol.* (1993) 150:896-908.

Kondo et al., "Rationale for a novel immunotherapy of cancer with allogeneic lymphocyte infusion" *Med. Hypotheses* (1984) 15:241-277.

Kriegler et al. A novel form of TNF/cachectin is a cell surface cytotoxic transmembrane protein: ramifications for the complex physiology of TNF. *Cell* 53:45, 1988.

Kruse et al., "Analysis of interleukin 2 and various effector cell populations in adoptive immunotherapy of 9L rat gliosarcoma: Allogeneic cytotoxic T lymphocytes prevent tumor take" *Proc. Natl. Acad. Sci. USA* (1990) 87:9577-9581.

Kruse et al., "Intracranial administrations of single or multiple source allogeneic cytotoxic T lymphocytes: chronic therapy for primary brain tumors" *J. Neuro-Oncol.* (1994) 19:161-168.

Kruse et al., "Systemic chemotherapy combined with local adoptive immunotherapy cures rats bearing 9L gliosarcoma" *J. NeurooncoL* (1993) 15:97-112.

Lange, et al., "A Pilot Study of the Combination of Interleukin-2-Bases Immunotherapy and Radiation Therapy." *Journal of Immunology* 12:265-271 (1992).

Lesham et al. *Cancer Immunol. Immunotherap.* (1984) vol. 17:117-123.

Li Xu, et al, "Factors Affecting Long-Term Stability of Moloney Murine Leukemia Virus-Based Vectors". Virology 171:331-341 (1989).

Lotze et al., "Gene therapy of cancer: a pilot study of IL-4-gene-modified fibroblasts admixed with autologous tumor to elicit an immune response" *Human Gene Therapy* (1994) 5:41-5 5.

Lotze, Michael T. and Finn, Olivera J., "Recent Advances in Cellular Immunology: Implication for Immunity to Cancer." *Immunotherapy Today* 11:190-193 (1990).

Lotze, Michael T. et al., "Mechanisms of Immunologic Antitumor Therapy: Lesson from the Laboratory and Clinical Applications." Fundamental Immunology, Second Edition. 923-942 (1989).

Lotze, Michael T. et al., "High-Dose Recombinant Interleukin 2 in the Treatment of Patients with Disseminated Cancer." *JAMA* 256:3117-3124 (1986).

Mackensen et al., "Immunostimulatory cytokines in somatic cells and gene therapy of cancer" *Cytokine & Growth Factor Reviews* (1997) 8:119-128.

Mackensen et al., "Induction of tumor-specific cytotoxic T lymphocytes by immunization with autologous tumor cells and interleukin-2 gene transfected fibroblasts" *J. Mol. Med* (1997) 75:290-296.

Malcolm S Mitchell, Combining Chemotherapy and Biomodulation in the Treatment of Cancer, in Human Tumor Antigens and Specific Tumor Therapy, UCLA Symposium at Keystone Colorado 91345-358 (Metzgar and Mitchell ed., 1989).

Matsumoto et al., "Recombinant Human Granulocyte Colony-Stimulating Factor Inhibits the Metastasis of Hematogenous and Non-Hematogenous Tumors in Mice." *Int. J. Cancer* 49:444-449(1991).

McBride and Dougherty, "Radiotherapy for genes that cause cancer" *Nature Medicine* 1:1215-1217 (1995).

McBride et al. "Interleukin-3 in Gene Therapy of Cancer," Folia Biologica, vol. 40:62-73, Feb. 1994.

McBride et al., "Modification of Tumor Microenvironment by Cytokine Gene Transfer." *Acta Oncologica* 34:447-451 (1995).

McDonald et al., "Combined Betaseron R (Recombinant Human Interferon Beta) and Radiation for Inoperable Non-Small Cell Lung Cancer." *Int. J. Radiation Oncology Biol. Phys.* 27:613-619, 1993.

Mertelsmann et al., "Pilot study for the evaluation of T-cell mediated tumor immunotherapy by cytokine gene transfer in patients with malignant tumors" *J. Mol Med* (1995) 73:205-206.

Mitchell et al, "Active specific immunotherapy of melanoma with allogeneic cell lysates. Rationale, results, and possible mechanisms of action" *Ann. N.Y. Acad. Sci.* (1993) 690:153-166.

Mitchell, et al., "Combining Chemotherapy and Biomodulation in the Treatment of Cancer," Human Tumor Antigens and Specific Tumor Therapy, UCLA Symposium at Keystone Colorado. Ed., Metzgar, et al., New York: Alan R. Liss, Inc., 1989, vol. 99, pp. 345-358.

Ogura, Hiromi et al., Implantation of Genetically Manipulated Fibroblasts into Mice as Antitumor. Alpha-Interferon Therapy. *Cancer Research* 50:5101-5106 (1990).

Patchen et al., "Mast cell growth factor (C-kit ligand) in combination with granulocyte-macrophage colony-stimulating factor and interleukin-3: in vivo hemopoietic effects in irradiated mice compared to in vitro effects," *Biotherapy*, vol. 7:13-26, Jul. 1994.

Peace, David J et al., "T Cell Recognition of Transforming Proteins Encoded by Mutated ras Proto-Oncogenes." *J. Immunology.* 146:2059-2065 (1991).

Perez et al. A nonsecretable cell surface mutant of tumor necrosis factor (TNF) kills by cell to cell contact. *Cell* 63:251, 1990.

Pizza, G. et al., "Intra-Lymphatic Administration of Interleukin-2 (IL-2) in Cancer Patients: A Pilot Study." *Lympokine Research* 7:45-48 (1988).

Plaskin et al., "Effective anti-metastatic melanoma vaccination with tumor cells transfected with MHC genes and/or infected with newcastle disease virus (NDV)" *Int. J. Cancer* (1994) 59:796-801.

Press Release, Immune Response Corporation, Feb. 22, 2000. The Immune Response Corporation announces preclinical results for a genetically engineered cancer vaccine.

Press Release, Immune Response Corporation, Oct. 11, 1999. The Immune Response Corporation reports investigational colon cancer vaccine Phase I trial data in *Clinical Cancer Research*.

Redd et al., "Allogeneic tumor-specific cytotoxic T lymphocytes" *Cancer Immunol. Immunother.* (1992) 34:349-354.

Rosenberg, Steven A. "The Immunotherapy and Gene Therapy of Cancer." *J. Clin. Oncology* 10:180-199 (1992).

Zarling et al., "Generation of cytotoxic T lymphocytes to autologous human leukemia cells by sensitization to pooled allogeneic normal cells" *Nature* (1978) 274: 269-271.

Zatloukalet al., "Elicitation of a systemic and protective anti-melanoma immune response by an IL-2-based vaccine" *The Journal of Immunology* (1995) 154:3406-3419.

Zhang et al. "Gene Therapy strategies for cancer," *Expert Opinion on Investigational Drugs*, vol. 4 (6):487-514, Jun. 1995.

\* cited by examiner

PHARMACEUTICAL COMPOSITION FOR CANCER TREATMENT CONTAINING CELLS THAT EXPRESS A MEMBRANE CYTOKINE

REFERENCE TO RELATED APPLICATIONS

This application is a divisional of U.S. application Ser. No. 08/901,225, filed Jul. 24, 1997, now U.S. Pat. No. 6,277,368, which application claims the priority benefit of provisional U.S. application Ser. Nos. 60/023,108, filed Jul. 25, 1996, now abandoned; and 60/029,286, filed Oct. 29, 1996, now abandoned. The afore-listed applications are hereby incorporated herein by reference in their entirety.

FIELD OF THE INVENTION

The present invention relates generally to the fields of cellular immunology and cancer therapy. More specifically, it relates to the generation of an anti-tumor immune response in a human by administering a cellular vaccine, comprising cells genetically altered to secrete a cytokine, in combination with a source of tumor antigen.

BACKGROUND

In spite of numerous advances in medical research, cancer remains a leading cause of death throughout the developed world. Non-specific approaches to cancer management, such as surgery, radiotherapy and generalized chemotherapy, have been successful in the management of a selective group of circulating and slow-growing solid cancers. However, many solid tumors are considerably resistant to such approaches, and the prognosis in such cases is correspondingly grave.

One example is brain cancer. Each year, approximately 15,000 cases of high grade astrocytomas are diagnosed in the United States. The number is growing in both pediatric and adult populations. Standard treatments include cytoreductive surgery followed by radiation therapy or chemotherapy. There is no cure, and virtually all patients ultimately succumb to recurrent or progressive disease. The overall survival for grade IV astrocytomas (glioblastoma multiforme) is poor, with ~50% of patients dying in the first year after diagnosis.

A second example is ovarian carcinoma. This cancer is the fourth most frequent cause of female cancer death in the United States. Because of its insidious onset and progression, 65 to 75 percent of patients present with tumor disseminated throughout the peritoneal cavity. Although many of these patients initially respond to the standard combination of surgery and cytotoxic chemotherapy, nearly 90 percent develop recurrence and inevitably succumb to their disease.

Because these tumors are aggressive and highly resistant to standard treatments, new therapies are needed.

An emerging area of cancer treatment is immunotherapy. The general principle is to confer upon the subject being treated an ability to mount what is in effect a rejection response, specifically against the malignant cells. There are a number of immunological strategies under development, including: 1. Adoptive immunotherapy using stimulated autologous cells of various kinds; 2. Systemic transfer of allogeneic lymphocytes; 3. Intra-tumor implantation of immunologically reactive cells; and 4. Vaccination at a distant site to generate a systemic tumor-specific immune response.

The first of the strategies listed above, adoptive immunotherapy, is directed towards providing the patient with a level of enhanced immunity by stimulating cells ex vivo, and then readministering them to the patient. The cells are histocompatible with the subject, and are generally obtained from a previous autologous donation.

One approach is to stimulate autologous lymphocytes ex vivo with tumor-associated antigen to make them tumor-specific. Zarling et al. (1978) *Nature* 274:269-71 generated cytotoxic lymphocytes in vitro against autologous human leukemia cells. Lee et al. (1996) abstract, *Gastroenterology* conducted an in vitro mixed lymphocyte culture with inactivated leukemic blast cells and autologous lymphocytes, and generated effector T lymphocytes cytotoxic for a tumor antigen on autologous blast cells. An MHC D-locus incompatibility was thought to be necessary to provide proper help in the lymphocyte culture. Lesham et al. (1984) *Cancer Immunol. Immunother.* 17:117-23 developed cytotoxic responses in vitro against murine thymoma cells by allosensitization.

Gately et al. (1982) *J. Natl. Cancer Inst.* 69:1245-54 found that 5 out of 9 human glioma cell lines did not elicit allogeneic cytolytic lymphocyte responses in ex vivo cultures. However, if inactivated, allogeneic lymphocytes were provided as stimulator cells in the cultures, tumor-specific cytolytic T lymphocytes and non-specific non-T effectors were generated to 4 of the nonstimulatory lines. In U.S. Pat. No. 5,192,537, Osband suggests activating a tumor patient's mononuclear cells by culturing them ex vivo in the presence of tumor cell extract and a non-specific activator like phytohemagglutinin or IL-1, and then treating the culture to deplete suppresser cell activity.

Despite these experimental observations, systemic administration of ex vivo-stimulated autologous tumor-specific lymphocytes has not become part of standard cancer therapy.

Autologous lymphocytes and killer cells may also be stimulated non-specifically. In one example, Fc receptor expressing leukocytes that can mediate an antibody-dependent cell-mediated cytotoxicity reaction are generated by culturing with a combination of IL-2 and IFN-γ U.S. Pat. No. 5,308,626. In another example, peripheral blood-derived lymphocytes cultured in IL-2 form lymphokine-activated killer (LAK) cells, which are cytolytic towards a wide range of neoplastic cells, but not normal cells. LAK are primarily derived from natural killer cells expressing the CD56 antigen, but not CD3. Such cells can be purified from peripheral blood leukocytes by IL-2-induced adherence to plastic (A-LAK cells; see U.S. Pat. No. 5,057,423). In combination with high dose IL-2, LAK cells have had some success in the treatment of metastatic human melanoma and renal cell carcinoma. Rosenberg (1987) *New Engl. J. Med.* 316:889-897. This strategy is labor-intensive, costly, and not suited to all patients. Schwartz et al. (1989) *Cancer Res.* 49:1441-1446 showed that A-LAK cells are superior to LAK cells at reducing lung and liver metastases of breast cancer in experimental animal models, but this was not curative and there were no long-term survivors.

For examples of trials conducted using LAK in the treatment of brain tumors, see Merchant et al. (1988) *Cancer* 62:665-671 & (1990) *J. Neuro-Oncol.* 8:173-198; Yoshida et al. (1988) *Cancer Res.* 48:5011-5016; Barba et al. (1989) *J. Neurosurg.* 70:175-182; Hayes et al. (1988) *Lymphokine Res.* 7:337-345; and Naganuma et al (1989) *Acta Neurochir.* (Wien) 99:157-160. Another study proposes therapy for recurrent high-grade glioma using autologous mitogen-activated and IL-2 stimulated (MAK) killer lymphocytes, in combination with IL-2. Jeffes et al. (1991) *Lymphokine Res.*

10:89-94. While none of these trials was associated with serious clinical complications, efficacy was only anecdotal or transient. Induction of tumor-specific immunity in patients receiving such treatments has not been shown.

Another form of adoptive therapy using autologous cells has been proposed based on observations with tumor-infiltrating lymphocytes (TIL). TILs are obtained by collecting lymphocyte populations infiltrating into tumors, and culturing them ex vivo with IL-2. Finke et al. (1990) Cancer Res. 50:2363-2370 have characterized cytolic activity of CD4+ and CD8+TIL in human renal cell carcinoma. TILs have activity and tumor specificity superior to LAK cells, and have been experimentally administered, for example, to humans with advanced melanoma. Rosenberg et al. (1990) New Engl. J. Med. 323:570-578. The effector population within TILs may be cytotoxic T lymphocytes (CTL) which are primed to be tumor-specific in the host and are devoid of lytic granules, and become transformed into cytolytic lymphoblasts when stimulated in culture. Berke et al. (1988) J. Immunol. 129:303 ff. Unfortunately, TILs can only be prepared in sufficient quantity to be clinically relevant in a limited number of tumor types. These strategies remain experimental, especially in human therapy.

The second of the strategies for cancer immunotherapy listed earlier is adoptive transfer of allogeneic lymphocytes. The rationale of this experimental strategy is to create a general level of immune stimulation, and thereby overcome the anergy that prevents the host's immune system from rejecting the tumor. Strausser et al. (1981) J. Immunol. Vol. 127, No. 1 describe the lysis of human solid tumors by autologous cells sensitized in vitro to alloantigens. Zarling et al. (1978) Nature 274:269-71 demonstrated human anti-lymphoma responses in vivo following sensitization with allogeneic leukocytes. Kondo et al. (1984) Med Hypotheses 15:241-77 observed objective responses of this strategy in 20-30% of patients, and attributed the effect to depletion of suppressor T cells. The studies were performed on patients with disseminated or circulating disease. Even though these initial experiments were conducted over a decade ago, the strategy has not gained general acceptance, especially for the treatment of solid tumors.

The third of the immunotherapy strategies listed earlier is intra-tumor implantation. This is a strategy directed at delivering effector cells directly to the site of action. Since the transplanted cells do not circulate, they need not be histocompatible with the host. Intratumor implantation of allogeneic cells may promote the ability of the transplanted cells to react with the tumor, and initiate a potent graft versus tumor response.

Kruse et al. (1990) Proc. Natl. Acad Sci. U.S.A. 87:9577-9581 demonstrated that direct intratumoral implantation of allogeneic cytotoxic T lymphocytes (CTL) into brain tumors growing in Fischer rats resulted in a significant survival advantage over other populations of lymphocytes, including syngeneic CTL, LAK cells, adherent-LAK cells or IL-2 alone. Redd et al. (1992) Cancer Immunol. Immunother. 34:349-354 developed cytotoxic T lymphocytes specific for an allogeneic brain tumor in rats. The lymphocytes were specific for a determinant expressed only by the tumor, and were predicted to be useful for therapeutic purposes in vivo. Kruse et al. (1994) J. Neurooncol. 19:161-168 prepared CTLs from four MHC incompatible rat strains, and used them to treat Fischer rats bearing established 9L brain tumors. CTL were administered on a biweekly schedule, a different MHC incompatible CTL preparation being administered each time. Animals without tumor showed minimal localized brain damage. Those with tumors either showed: a) mononuclear cell infiltration, massive tumor necrosis beginning 2-4 days after treatment, and total tumor destruction by 15 days; or b) cellular infiltration, early tumor destruction, and then tumor regrowth progressing to death of the animal. Tumor regressor animals were resistant to intracranial rechallenge with viable tumor cells. Kruse et al. (1994). Intratumor CTL implants may optionally be combined with chemotherapy using cyclophosphamide. Kruse et al. (1993) J. Neurooncol. 15:97-112.

Despite the promise of intratumor implantation techniques, several caveats remain. First, implantation is frequently performed by surgical techniques, which may be too invasive for routine maintenance. Second, the strategy is directed at generating a local response, and may not be effective against metastases. Finally, the techniques remain unproved for use in human therapy.

The fourth of the immunotherapy, strategies listed earlier is the generation of an active systemic tumor-specific immune response of host origin. The response is elicited from the subject's own immune system by administering a vaccine composition at a site distant from the tumor. The specific antibodies or immune cells elicited in the host as a result will hopefully migrate to the tumor, and then eradicate the cancer cells, wherever they are in the body.

Various types of vaccines have been proposed, including isolated tumor-antigen vaccines and anti-idiotype vaccines. Mitchell et al. (1993) Ann. N.Y. Acad. Sci. 690:153-166 have treated cancer patients with mechanical lysates from a plurality of allogeneic melanoma cell lines, combined with the adjuvant DETOX™. These approaches are all based on the premise that tumors of related tissue type all share a common tumor-associated antigen. For patients with tumors that did not acquire expression of the antigen during malignant transformation, or that subsequently differentiated so as not to express it, none of these vaccines will be successful.

An alternative approach to an anti-tumor vaccine is to use tumor cells from the subject to be treated, or a derivative of such cells. For review see, Schimnacher et al. (1995) J. Cancer Res. Clin. Oncol. 121:487-489. In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells. The cells may optionally be cryopreserved, and the immune system may be monitored by skin testing. This approach does not solve the well-established observations that many tumors-are not naturally immunogenic. Many patients from which tumors have been resected are either tolerant or unable to respond to their own tumor antigen, even when comprised in a vaccine preparation.

Several ways of preparing autologous or syngeneic tumor cells have emerged that potentially enhance immunogenicity. Tumor cells may be combined with extracts of bacillus Calmette-Guerin (BCG) or the A60 mycobacterial antigen complex. Berd et al. (1990) J. Clin. Oncol. 8:1858-67; Maes et al. (1996) J. Cancer Res. Clin. Oncol. 122:296-300. Tumor cells may be lysed by or mixed with vaccinia virus. Hersey et al.; Ito et al. Tumor cells may be incubated with the Newcastle Disease Virus (NDV). U.S. Pat. No. 5,273,745. Autologous tumor cells may also be conjugated to haptens like dinitrophenyl. U.S. Pat. No. 5,290,551.

In another approach to increase immunogenicity, Guo and coworkers (WO 95/16775) suggest that tumor cells be fused with membrane components of a second cell that has a greater immunogenic potential. Suitable cells are an activated antigen-presenting cell such as a B cell. The fusion partner cell may be genetically altered to express an MHC protein, adhesion protein, or a cytokine. Rat hepatocarcinoma cells lost tumorigenicity when fused with syngeneic B cells, and were capable of eliciting a T-cell response. Rats injected with the hybrid cells generated CD4+ and CD8+ T cells against subsequent challenge, or eradicated preexisting tumors via a CD8+ T cell mediated mechanism.

In yet another approach, autologous or syngeneic tumor cells are genetically altered to produce a costimulatory molecule. Examples of costimulatory molecules include cell surface receptors, such as the B7-1 costimulatory molecule or allogeneic histocompatibility antigens. Salvadori et al. (1995) *Hum. Gene Ther.* 6:1299-1306; Plaksin et al. (1994) *Int. J. Cancer* 59:796-801; EP 56967.

Other examples are secreted activators, including cytokines. For review see, Pardoll et al. (1992) *Curr. Opin. Immunol.* 4:619-23; Saito et al. (1994) *Cancer Res.* 54:3516-3520; Vieweg et al. (1994) *Cancer Res.* 54:1760-1765; Gastl et al. (1992) *Cancer Res.* 52:6229-6236; and WO 96/07433). Tumor cells have been genetically altered to produce TNF-α, IL-1, IL-2, IL-3, IL-4, IL-6, IL-7, IL-10, IFN-α, IFN-γ and GM-CSF. Asher et al. (1991) *J. Imunol.* 146:3227-3234; Blankenstein et al. (1991) *J. Exp. Bed.* 173:1047-1052; Karp et al. (1993) *J. Imunol* 150:896-908; Douvdevani et al. (1992) *Int. J. Cancer* 51:822-830; Cavallo et al. (1992) *J. Immunol.* Vol. 149: 3627-3635 No. 11 & (1993) *Cancer Res.* 53:5067-5070; Fearon et al. (1990) *Cell* 60:397-403; Gansbacher et al. (1990) *J. Exp. Med.* 172:1217-1224; Connor et al. (1993) *J. Exp. Med.* Vol. 177:1127-1134; Topalian et al. (1988) *J. Clin. Oncol.* 6:838-853; McBride et al. (1992) *Cancer Res.* 52:3931-3937; Golumbek et al. (1989) *Science* 254:713 ff & (1991) *Science* 254:713-716; Tepper et al. (1989) *Cell* 57:503-512; Santin et al. (1995b); Santin et al. (1995c) *Int. J. Gynecol. Cancer* 5:401-410; *Gynecol. Oncol.* 58:230-239; Santin (1996) *Am. J. Obst. Gynecol.* 174:633-639; Allione et al. (1994) *Cancer Res.* 54:6022-6026; EP 538952; Belldegrun et al. (1993) *J. Natl. Cancer Inst.* 85:207-216; Dranoff et al. (1993) *Proc. Natl. Acad. Sci USA* Vol. 90:3539-3543.

Golumbek et al. (1989) reported that mouse renal carcinoma cells inserted with a gene for IL-4 was strongly immunogeneic for systemic T cell immunity, and protected mice against a subsequent lethal challenge with unmodified, parental tumor cells. Induction of an immune response does not depend on inherent immunogenicity; cytokines like IL-2 induce a response that is protective against otherwise non-immunogenic adenocarcinoma cells, including distant metastases. Cavallo et al. 1991 & 1992. Antitumor immunity is intensified by a cancer vaccine that produces both GM-CSF and IL-4. Wakimoto et al. (1996) *Cancer Res.* 56:1828-33. The cytokine or cytokine combination may recruit or stimulate cells of the immune system, and thereby overcome the normal barrier to immunity. Certain cytokines also affect the expression of major histocompatibility molecules and intercellular adhesion molecules by cancer cells (Santin et al. 1995a, *Int. J. Cancer* 65:688-694), potentially improving immunogenicity.

The experiments with transduced histocompatible tumor cells have been done chiefly in genetically restricted animal models, which are not directly equivalent to a heterogeneous human patent population. Colombo et al. (1995) *Cancer Immunol. Immunother.* 41:265-270. Not all cancer types are responsive to the same cytokines. There are concerns about injecting human patients with replication-competent tumor cells, particularly after genetic alteration. In addition, there is usually not enough time to genetically alter and grow up sufficient cells of the the patient to be treated for use in a vaccine.

Blumbach (WO 96/05866) has suggested vaccines of live tumor cells transduced with: a) a gene coding for an immunostimulatory protein; b) a cytokine; and c) a thymidine kinase gene. The composition is provided as live cells which can grow in vivo and stimulate a response, and then be selectively killed via the thymidine kinase. The possibility of escape mutants is likely to be a subject of regulatory concern for this approach in human therapy. Golumbek et al. (1992) *J. Immunother.* 12:224-230 have shown that proliferating tumor cells with suicide genes can also survive toxin treatment when they exit the cell cycle temporarily or are sequestered pharmacologically.

As an alternative, Cohen (WO 95/31107) suggested that neoplastic disease can be treated with a cellular immunogen comprising allogeneic cells genetically altered to express one or more cytokines, and also to express tumor-associated antigens encoded by autologous genomic tumor DNA. In this approach, an allogeneic cell (exemplified as a mouse LM cell) is genetically altered to express: a) a cytokine; and b) a tumor-associated antigen autologous to the subject to be treated. Accordingly, the vaccine need not comprise live tumor cells.

However, application of the Cohen invention to human subjects would require prior knowledge for each patient of a particular tumor-associated antigens expressed by the particular tumor. Many human cancers of widespread clinical interest do not have reliable commonly-shared markers. Once a relevant marker is identified for a particular patient, a cell line must be engineered accordingly, and cultured to the required density prior to treatment. Thus, each patient would become their own research and development project. Since the immune response would be focused only at the particular tumor-associated antigen used, it may be less effective than one directed against the spectrum of antigen expressed by a complete tumor cell. Furthermore, the vaccine comprises a live genetically altered cell line, raising the concerns outlined earlier. Cohen demonstrated only a modest improvement in survival in the animal studies, and failed to provide any evidence that his formulation would be effective in human cancer patients.

A suitable strategy for a human anti-tumor cellular vaccine has to contend with the following problems: a) heterogeneity amongst tumors (even tumors of the same type) in the display of tumor-associated antigens; b) heterogeneity in the immune response between individuals with regards to both antigens and cytokines; c) ethical and regulatory concerns about compositions that may be used in humans; and d) lack of development time in most clinical settings, limiting the ability to engineer new cell lines or otherwise tailor the vaccine to each patient.

SUMMARY OF THE INVENTION

This invention provides compositions and methods for eliciting an anti-tumor immune response in a human patient in need thereof. The compositions of the invention are cells or cell mixtures in a compatible excipient, and are referred to herein as a vaccine or an immunogenic composition. They may be administered to patients either to treat or palliate a clinically detectable tumor, or for prophylaxis, particularly after surgical debulking, chemotherapy or radiation therapy of a previously detectable tumor. The compositions are typically administered at a location distant from the original tumor, with the objective of stimulating a systemic reactivity against the tumor. The reactivity may in turn eradicate or slow the development of tumor cells, either at the primary site, within metastases (if there are any), or both.

Minimally, the vaccines of this invention comprise two components. The first is a source of tumor antigen, preferably a plurality of antigens, which is associated with the cancer for which the patient is at risk. A convenient source of tumor-associated antigen is tumor cells previously obtained from the patient, such as during surgical resection. The second component is a cytokine producing cell capable of stimulating the patient's immune system to produce an anti-tumor response.

In one series of preferred embodiments, the cytokine producing cell is a cell from an allogeneic donor, typically a tumor cell and preferably a tumor cell of the same type as the subject being treated, that has been genetically altered to express the cytokine at an elevated level. A preferred source of tumor antigen is the patient, and the vaccine is typically assembled by mixing tumor cells from the patient (or antigen therefrom) with the allogeneic cytokine-producing cells.

In another series of preferred embodiments, the cytokine producing cell is a cell that is autologous or syngeneic to the patient that has been genetically altered to produce a cytokine. Typically, the cell will be a cell obtained from the patients tumor (or its progeny) that was subsequently altered so as to produce an effective amount of the cytokine. In this form, the same cell provides both components necessary to evoke the desired response: i.e., both the tumor antigen and the stimulatory cytokine.

Cytokines useful for expression by the cytokine-producing cells according to either of these series of embodiments include those that promote immunostimulation against the tumor antigen by any mechanism. Preferred and non-limiting examples are IL-4, GM-CSF, IL-2, TNF-α, and M-CSF. In certain embodiments, the cytokine is primarily secreted by the cell. In other embodiments, the cytokine is produced by the cell as a transmembrane protein, and provides immunostimulation by a mechanism that may involve intercellular contact. Transmembrane cytokines include those such as mM-CSF, that naturally occur in a transmembrane form and cytokines that naturally occur in a secreted form that are engineered to incorporate a region that allows them to be retained in the cell membrane.

Also embodied in this invention are compositions and methods for treating a neoplastic disease such as cancer, comprising administering any one of the compositions or vaccines of this invention, or eliciting an anti-tumor immunological response according to any one of the methods of this invention. The treatment is effective in palliating the disease condition according to any clinically acceptable criteria for improvement, such as inhibition of tumor growth, increase in life expectancy of the patient, or improvement in quality of life or performance activity score.

Further embodiments of the invention include kits and methods for assembling the immunological and pharmaceutical compositions of this invention for use according to the descriptions provided in this disclosure.

BRIEF DESCRIPTION OF THE FIGS.

FIG. 1 is a two-panel graph depicting the growth properties (Panel A) and cytokine secretion (Panel B) by an ovarian cancer cell line genetically altered to express IL-4, designated UCI 107E IL-4 GS.

FIGS. 2A-C are graphs showing the effects of irradiation on the IL-4 secreting tumor cell line UC1 107E IL-4 GS. FIG. 2A shows the growth pattern of cells given 5,000 (□) or 10,000 (■) rads. FIGS. 2B & 2C show IL-4 detected by ELISA in the culture medium expressed as total concentration (FIG. 2B) or per cell (FIG. 2C) Various times after irradiation.

FIGS. 3A-C are a series of FACS analysis profiles (incidence versus fluorescence intensity) revealing expression of various surface antigen by UCI 107E IL-4 GS, before or after irradiation with 5,000 or 10,000 rads.

Figure 7:
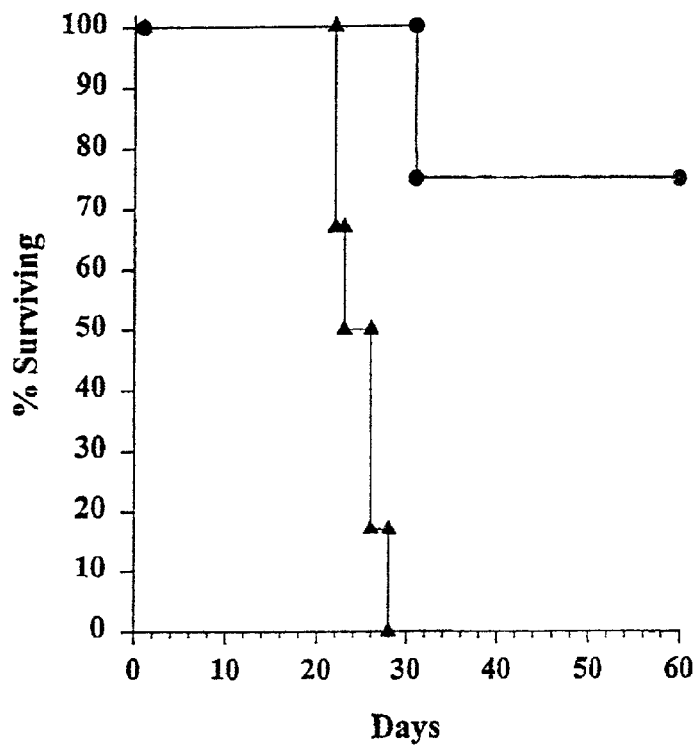
Figure 7:
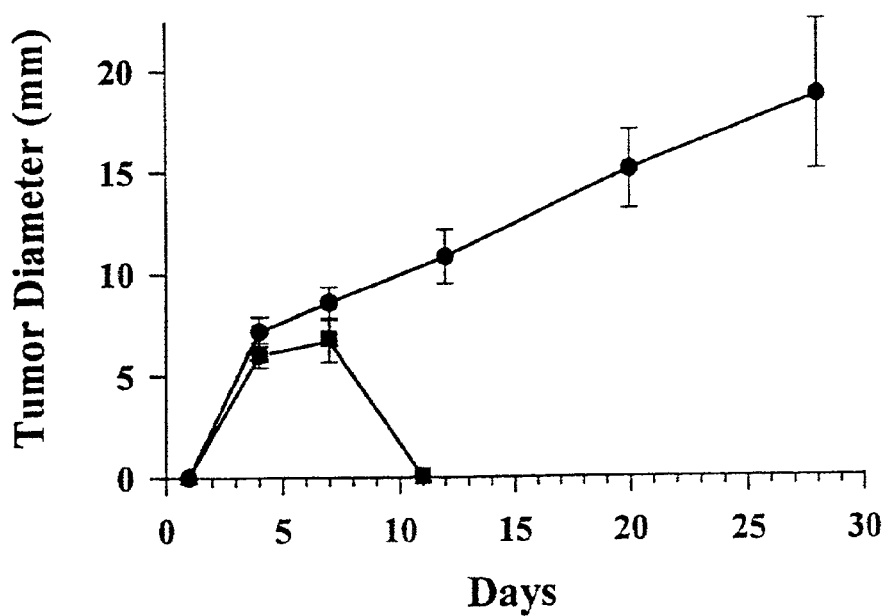

FIG. 7 is two-panel graph showing that syngeneic glioblastoma cells expressing membrane M-CSF induce a systemic cell-mediated immunity in animals. The Upper Panel shows that splenocytes transfer tumor resistance between animals (●) unless depleted using anti-T-lymphocyte antibody (▼). The Lower Panel shows that administration of the M-CSF expressing cell line (■) but not vector control cells (●) at a site outside the brain causes regression of the tumor cells injected subcutaneously.

DETAILED DESCRIPTION

A central feature of the cellular vaccines of this invention is the use of multiple components that act in concert once inside the host to produce the desired effect. In other words, the strategy is more than just an injection of cancer cells.

The strategy is a significant departure from previous approaches to cancer immunotherapy in humans. Several important embodiments of this invention differ from other compositions comprising cancer cells, in that it contains separately: a) tumor associated antigen; and b) a cytokine expressing cell line that acts in trans to induce a beneficial response against the antigen.

Tumor antigen is preferably provided from a cancer cell or the progeny thereof, preferably a cell autologous to the subject to be treated, typically obtained from the subject either by surgical resection, biopsy, blood sampling, or other suitable technique. The cytokine-producing cell is from a different donor which is genetically altered and characterized ahead of time for properties relating to its ability to stimulate an enhanced immune response when used in a vaccine of this invention. The genetically altered cell is allogeneic to the subject being treated, and is typically the same type of cancer as is borne by the subject.

A separately filed patent application shows that mixed lymphocytes implanted directly into a tumor bed limits or even reverses tumor growth. These experiments and results are described in a PCT patent application published as WO 96/29394 (corresponding to PCT/US96/03621), which is hereby incorporated herein by reference in its entirety. The effect on tumor mass appeared in part to be due to an active immunological reaction of host origin, which appears to be a long-lasting one. It was hypothesized that increased expression transplantation antigens stimulated by allogeneic lymphocytes in the implant resulted in the massive recruitment of lymphoid cells near the tumor site, and that certain of the recruited cells played a role in reacting specifically against the tumor. A significant element of this hypothesis is that the cells stimulating the host immune response (the mixed lymphocytes) are different from the source of tumor antigen, but lead to reactivity against tumor antigen.

Observations of this kind contributed partly to the inspiration for additional vaccine compositions. A second-generation vaccine would encompass a number of improvements over previously disclosed compositions. Desirable improvements include:

a composition that could stimulate an active response against a plurality of tumor-associated antigens in any subject treated;

the ability to prepare a vaccine without preculturing of the subject's cells, preferably at the instant that tumor cells are available from the subject;

the use of cells of minimal proliferative capacity;

a well-defined and reproducible immunostimulatory capacity;

the ability to tailor the immunostimulatory capacity to the patient, as required; and a capability to administer the vaccine at a site distant from the primary tumor, preferably with minimal invasiveness.

In order to meet these requirements, it was decided that the immunostimulatory cells and the source of tumor antigen should be different. Cells genetically altered to produce cytokines are strongly immunostimulatory. When cells are obtained from a donor other than the subject, they can be genetically altered in advance, cloned to stabilize the characteristics, selected for high levels of expression, and further selected for an ability to express cytokines even after inactivation. This eliminates the need to culture each autologous cell line, and has the benefit of careful standardization and quality control. The fact that the immunostimulatory cells are typically HLA-incompatible is probably irrelevant, since their main role is to initiate an immunological reaction in the host, which can then mature after the immunostimulatory cells are depleted. HLA-incompatibility can even be an advantage in the immunostimulatory potential of the cells.

Stimulation is provided to generate an immune reaction against tumor antigen as a bystander. When used in an implant setting, a nexus of tumor antigen is supplied by residual primary tumor cells. For a systemic or distally administered composition, it is necessary to provide the nexus of tumor antigen by mixing it into the preparation. Preferably, a plurality of tumor antigen associated with the subject's own tumor is used. This is conveniently provided by using cells obtained from the subject's tumor, progeny thereof, or an extract of either the primary tumor cells or their progeny. These cells may also be inactivated, since they generally do not need to proliferate to provide tumor antigen. Using autologous tumor cells confers the additional advantage of being HLA-compatible, meaning the cells may persist near the injection site or at another site of ongoing immunological activity, to assist in the maturation of the response.

A hallmark of the cellular vaccines of the present invention is that the effect is substantially greater than is obtained using tumor cells alone, or tumor cells mixed with previously used adjuvants or cofactors. Interaction between the tumor cells and the stimulated lymphocytes of the vaccines is probably complex. While not wishing to be bound by theory, it is envisaged that the cytokine expressed by the genetically altered cell is effective in recruitment, activation, or stimulating the interaction of host immune cells. The recruited and stimulated host cells may then respond to atypical (but otherwise less immunogenic) components in the vicinity, including any antigens present upon or within or secreted by the autologous tumor cells. The cytokine-producing cells may also play a role in promoting antigen processing and presentation, or provide co-stimulation for antigen being presented. In addition, the cytokine-producing cells may also provide specific immunostimulation in cis for the tumor antigens expressed by the cytokine-producing cells. Accordingly, in certain preferred embodiments of this application, the cells used to generate the cytokine-producing cells are derived from a tumor type that is closely related to that of the subject being treated.

An immunological response resulting from administration of the vaccine may comprise both humoral and cellular components, but a cellular response is especially preferred. Cellular immunity (either cytotoxic lymphocytes, or helper-inducer cells recruiting other effector mechanisms) are believed to be important in providing a specific effect against the cells of the target neoplasia. The presence of an immunological response may be monitored by standard immunological techniques. However, in human therapy, a primary objective is an improvement in the clinical condition of the patient. Clinical outcome is therefore a superior assay for the effectiveness of the compositions and methods of this invention when directed towards cancer treatment.

The present invention is superior to strategies used or suggested previously. Advantages of the vaccine compositions of this invention include the following:

The vaccines improve the clinical condition or prognosis of human cancer patients, even though tumor cells residing in cancer patients are apparently poorly immunogenic on their own.

Although the response is presumably mediated by a tumor-associated antigen, there is no need to confirm the presence of any particular antigen on the tumor of a treated subject. Use of patent's own tumor cells or an extract of such cells ensures a spectrum of relevant antigens.

There is no need to genetically alter patients' cells, or use patients' DNA to genetically alter cells of the vaccine.

The strategy is aimed at generating a long-lived systemic immune response, and may therefore be effective not only against the primary tumor, but also against metastatic cells sharing tumor antigen with the primary tumor.

With the exception of the initial sampling of the tumor cells, the protocol may be performed with minimally invasive procedures. The vaccine compositions are preferably administered at a site distant from the tumor. Subcutaneous routes of administration are preferred.

A particularly beneficial feature of certain vaccines of the invention is the fact that vaccine compositions can be tailored to particular cancer types, clinical features, and even to an individual subject, as necessary.

This is important where different tumor types respond to different cytokines and cytokine mixtures. For example, one tumor type can respond more frequently to IL-4 in combination with GM-CSF, whereas another tumor can respond to IL-4 in combination with TNF-α. Accordingly, a vaccine for the first tumor type is prepared by mixing cells genetically altered to express IL-4, and cells genetically altered to express GM-CSF with tumor-associated antigen from the subject to be treated. A vaccine for the second type is prepared by mixing cells expressing IL-4 with cells expressing TNF-α and tumor-associated antigen. There is no need to genetically alter a cell line to express multiple cytokines (although this is included in the invention) since lines expressing different cytokines may be combined. In another example, one tumor type can respond slightly better to IL-4 and GM-CSF at a 2:1 molar ratio, while another can respond slightly better to IL-4 and GM-CSF at a 1:2 molar ratio. The cells can be mixed together in a suitable proportion to provide a molar ratio suited for the tumor being treated. In a third example, the ratio of cytokine-secreting cells to tumor antigen or autologous tumor cells is also adjusted according to the tumor being treated.

Fine-tuning of the components of the vaccine can be done according to previous observations on the effectiveness of the vaccine in various clinical settings, in the context of features of the tumor in the subject being treated. A principal feature is the type of cancer being treated, with optional secondary features including, but not limited to, the location of the tumor in the body, staging, invasiveness, morphological features, results of biochemical tests for antigen expression or genetic alteration conducted on patient's serum or a tumor sample, clinical features, and response to previous therapy.

Fine-tuning the vaccine is an added benefit of the nature of the composition, but is not required. Many combinations of cytokine-producing cells and autologous tumor cells are effective, and are encompassed by the claimed invention. Effective combinations are readily determined by a practitioner of ordinary skill in the art by following the guidelines provided herein. The availability of a plurality of allogeneic cytokine-producing cells for admixing into a vaccine considerably facilitates not only the adjustment of the composition in accordance with previous experience, but also the initial testing of various potential combinations.

Other embodiments of this invention involve genetically altering a patient's own tumor cells so as to produce a stimulatory cytokine, especially a membrane-bound cytokine. The same cell thus provides both the cytokine and the tumor antigen. These cells can be administered alone, or are optionally mixed with allogeneic cells producing additional cytokines in order to increase stimulation, again providing an opportunity to fine-tune the relative amount and mixture of cytokines provided.

A further description of preferred ways to prepare and use the vaccine compositions of this invention are provided in the sections that follow.

Definitions

The terms "vaccine", "immunogen", or "immunogenic composition" are used herein to refer to a compound or composition, as appropriate, that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The vaccines, immunogens, and immunogenic compositions of this invention are active vaccines, which means that they are capable of stimulating a specific immunological response (such as an anti-tumor antigen or anti-cancer cell response) mediated at least in part by the immune system of the host individual. The immunological response may comprise antibody, immunoreactive cells (such as helper/inducer or cytotoxic cells), or any combination thereof, and is preferably directed towards an antigen that is present on a tumor towards which the treatment is directed. The response may be elicited or restimulated in a subject by administration of either single or multiple doses. Nothing further is required of a composition in order for it to qualify as a vaccine, unless otherwise specified.

A compound or composition is "immunogenic" if it is capable of either: a) generating an immune response against an antigen (such as a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

"Stimulating" an immune or immunological response refers to administration of a compound or composition that initiates, boosts, or maintains the capacity for the host's immune system to react to a target substance, such as a foreign molecule, an allogeneic cell, or a tumor cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in whom previous reactivity was detected; for example, due to natural immunity, spontaneous immunization, or treatment using one or several compositions or procedures.

A "cell line" or "cell culture" denotes higher eukaryotic cells grown or maintained in vitro. "Progeny" of a cell include any cells formed by cell division of a progenitor, either in vivo or in vitro. It is understood that the descendants of a cell may not be completely identical (either morphologically, genotypically, or phenotypically) to the parent cell.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transducing a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. It is preferable that the genetic alteration is inheritable by progeny of the cell, but this is not necessarily required for the practice of this invention, particularly when altered cells are used in a pharmaceutical composition without further proliferation. A cell is described as "genetically altered" if it has itself been subjected to genetic alteration, or if it is the progeny of a cell that was subjected to genetic alteration, providing it retains the alteration of the progenitor. A cell is said to be "inheritably altered" if a genetic alteration is present which is inheritable by progeny of the altered cell.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. The term "tumor-associated antigen" or "TAA" is used herein to refer to a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention.

A protein such as a cytokine is referred to as a "transmembrane" protein if it normally remains stably associated in the membrane of the cell in which it is produced. The term does not require any particular configuration of the protein in the lipid bilayer of the membrane.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An immunogenic amount is an amount sufficient in the subject group being treated (either diseased or not) to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Preferred quantities and cell ratios for use in an effective amount are given elsewhere in this disclosure.

An "individual" or "subject" is a vertebrate, preferably a mammal, more preferably a human. Non-human mammals include, but are not limited to, farm animals, sport animals, and pets.

General Techniques

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991). See also Gately et al., Lee et al., and Zarling et al. (infra) for examples of techniques in mixed lymphocyte cultures.

General procedures for the preparation and administration of pharmaceutical compositions are outlined in *Remington's Pharmaceutical Sciences* 18th *Edition* (1990), E. W. Martin ed., Mack Publishing Co., Pa.

All patents, patent applications, articles and publications mentioned herein, both supra and infra, are hereby incorporated herein by reference.

Preparation of Cellular Vaccines

The cellular vaccines of this invention are typically assembled by preparing each cell population or equivalent thereof in an appropriate fashion, combining the components, and optionally coculturing or storing cell mixtures before administration to a subject.

Tumor-associated antigen: The source of tumor-associated antigen is most usually a tumor cell or cell line that is close in phenotype to that for which the patient is being treated. Tumors from the same tissue type and with similar histological characteristics tend to share tumor-associated antigens. While the complete spectrum of antigens may vary between individual tumors, there is a substantial probability that at least one will be shared. Preferably, the tumor cells are histocompatible with the subject to be treated.

Generally, when it is possible to obtain tumor cells in advance from the subject to be treated, these cells are preferred as more likely to bear a full complement of relevant tumor-associated antigens. Circulating tumors such as leukemias and lymphomas may be readily sampled from peripheral blood. Otherwise, tumor cells are generally sampled by a surgical procedure, including but not limited to biopsy, or surgical resection or debulking. Tumor cells may also be collected from metastatic sites. Solid tumors may be dissociated into separate cells by physical manipulation optionally combined with enzymatic treatment with such proteases as collagenase and the like. The cells are then transferred into fresh medium. Cells may be stored until further use, for example, by freezing in liquid $N_2$. Optionally, and especially when the original tumor mass is small, it is preferable to expand the tumor cell population to ensure an adequate supply. Cells are cultured in a growth medium suitable for propagation, optionally supplemented with growth factors.

Preferably, a stable cell population comprising features of the tumor cells is obtained without further transformation, although transformation is permissible where required. The cell population can be optionally cloned to enhance its stability or refine its characteristics, although this is generally not necessary. Conditions for reliably establishing short-term cultures and obtaining at least $10^8$ cells from a variety of tumor types is described in Dillman et al. (1993) *J. Immunother.* 14:65-69. If possible, the original tumor cell preparation is used without proliferation, since it is possible that a critical tumor antigen will be lost through the proliferative process.

Cancer cells or cell lines obtained as described may be combined directly with the other components of the vaccine. However, it is preferable to inactivate the cancer cells to prevent further proliferation once administered to the subject. Any physical, chemical, or biological means of inactivation may be used, including but not limited to irradiation (preferably with at least about 5,000 cGy, more preferably at least about 10,000 cGy, even more preferably at least about 20,000 cGy); or treatment with mitomycin-C (preferably at least 10 µg/mL; more preferably at least about 50 µg/mL).

Cancer cells for use as a tumor antigen source may alternatively be fixed with such agents as glutaraldehyde, paraformaldehyde, or formalin. They may also be in an ionic or non-ionic detergent, such as deoxycholate or octyl glucoside, or treated, for example, using Vaccinia Virus or Newcastle Disease Virus. If desired, solubilized cell suspensions may be clarified or subject to any of a number of standard biochemical separation procedures to enrich or isolate particular tumor-associated antigens or plurality of antigens. Preferably, tumor antigen associated with the outer membrane of tumor cells, or a plurality of tumor associated antigens is enriched. The degree of enrichment may be 10-fold or more preferably 100-fold over that of a whole-cell lysate. Isolated antigens, recombinant antigens, or mixtures thereof may also be used. Before combination with other components of the vaccine, the tumor antigen preparation is depleted of the agent used to treat it; for example, by centrifuging and washing the fixed cells, or dialysis of the solubilized suspension. Preparation of tumor antigen, particularly beyond inactivation of the source tumor cell, may be viewed as optional and unnecessary for the practice of the embodiments of the invention, unless specifically required.

Cytokine-producing cells: The cellular vaccines of this invention also comprise a second cell population, of which at least a portion are cells producing a soluble or membrane-bound factor capable of potentiating an immunological response against the tumor-associated antigen or autologous cell of the vaccine.

Any cytokine or chemokine may be used for this purpose, especially those that have amongst their biological activities one or more of the following: a) the ability to recruit, enhance proliferation, enhance cytokine secretion by, or otherwise activate cells of the lymphocyte lineage; b) the ability to enhance uptake into antigen-presenting cells, the subsequent processing and display of antigen, or the concurrent production of cytokines; c) the ability to enhance display of histocompatibility antigens; d) the ability to enhance display of tumor-associated antigen by tumor cells; e) the ability to recruit other cells or soluble components that may participate in inflammation; or f) any other effect that results in a localized immune stimulation. The effect or effects can be measured in vitro according to standard immunological techniques, but should come into play in sufficient proximity to the tumor-associated antigen to provide an immunostimulatory effect that is at least partly specific for the antigen. A cytokine capable of mediating a plurality of the above-listed effects are particularly preferred.

Preferred cytokines include, but are not limited to, tumor necrosis factors, exemplified in TNF-α; interleukins, exemplified in IL-2, IL-4, IL-6, IL-7, and IL-10; interferons, exemplified in IFN-α and IFN-γ; hematopoetic factors; and colony stimulating factors, exemplified in GM-CSF and M-CSF. Different cytokines are more effective in certan cancers than others, and may vary between different cancers and patient groups. TNF and IL-2 are effective in cancers like adenocarcinoma in syngeneic animal vaccines, but less effective in ovarian or brain cancer, while M-CSF is especially potent in syngeneic animal vaccines for brain cancer.

Amongst the possible cytokines that can be used with this invention, GM-CSF and M-CSF are especially preferred because of their important role in the maturation and function of specialized antigen-presenting cells. This is believed to be important because many tumor cells, such as those of epithelial origin, do not express detectable MHC class II molecules. IL-4 is also preferred, as a pluripotent cytokine endowed of a broad range of stimulating activities on both B and T lymphocytes, as well as on hematopoietic cells. Its roles include the recruitment and activation of CD4+ antigen-presenting cells, as well as induction of cytotoxic T lymphocytes. TNF-α is a fourth cytokine which is preferred, in part because of its broad range of effects in the immune and inflammatory responses. Amongst cytokine combinations, the combination of GM-CSF and IL-4 is especially preferred. Embodiments of the invention with both of these cytokines are vaccines comprising autologous cancer cells and allogeneic cells genetically altered to express both GM-CSF and IL-4, or even more preferably vaccines comprising autologous cancer cells, allogeneic cells genetically altered to express GM-CSF, and different allogeneic cells genetically altered to express IL-4.

The majority of cytokine produced by the cells used in this invention may be secreted from the cells, or present on the outer membrane of the cells. Where the cytokine has a local immunostimulatory effect, it can be preferable that it be primarily attached to the cell membrane to keep it in the vicinity of bystander tumor antigen comprised in the vaccine. Where the cytokine has a recruitment effect, it can be preferable that it be primarily secreted. As a third option, the cytokine can be synthesized by the cell in both membrane-associated and secreted form. As illustrated in Example 5, the preferable form of a particular cytokine can be determined by simple side-by-side comparison. M-CSF may be used in either form, and in certain vaccine compositions may be more effective in the membrane-associated form. While not wishing to be bound by theory, it is possible that the membrane-associated form creates a bridge between the allogeneic tumor cell and antigen-presenting cells or responder lymphocytes; in effect a forced antigen presentation. M-CSF may have an advantage over many other cell-surface receptor ligands in this regard, because of an ability to simultaneously bridge cells, and provide a stimulatory signal through its cytokine effect.

Other cytokines that have both of these properties may be particularly effective in tumor vaccine compositions, and cells of the vaccine are preferably altered to express them in the membrane-associated form. Where particular cytokines have potent immunostimulatory activity but do not occur naturally in a membrane-bound form, it is possible to create a membrane-bound form as a fusion protein. Allogeneic cells are genetically altered with a vector comprising a cytokine encoding region and a transmembrane region in the same open reading frame, the transmembrane region being either upstream or downstream from the cytokine encoding region and optionally separated by an in-frame spacer region. The transmembrane region may be modeled on other known transmembrane proteins, or be an artificially designed polypeptide segment with a high degree of lipophillicity.

The protein and DNA encoding sequences of human IL-4 and TNF-α are known, and vectors comprising encoding sequences are available. For the IL-4 sequences and vectors, see U.S. Pat. No. 5,017,691and EP 230107. Genetically altered CHO cells are described in U.S. Pat. No. 5,034,133. The use of IL-4 (either as the isolated recombinant or in a genetically altered cell) in treating solid tumors are described in U.S. Pat. No. 5,382,427. TNF polypeptides, encoding sequences, vectors, and genetically altered host cells are described in U.S. Pat. No. 5,288,852, EP 155549, and U.S. Pat. No. 4,879,226. Variants of TNF, which may also be used in this invention, are described in U.S. Pat. No. 4,677,063. Compositions comprising TNF-α and interferon are taught in EP 131789. Synergism of TNF and IL-4 in the inhibition of cancer cell growth is described in WO 92/05805.

Other cytokines and cytokine-encoding polynucleotides are described further in the example section below, or may be readily obtained through publicly available biological deposits, or may be prepared according to publicly available disclosures.

The cell used to produce the cytokine for the vaccines of this invention is obtained from a different donor than the subject being treated. The donor is of the same species as the subject. Consequently, except in unusual circumstances, the cell is allogeneic to the subject. For the general practice of this invention, this definition is satisfied by at least one allelic difference at the amino acid level in a major histocompatibility complex (MHC) Class I or Class II antigen between the cytokine-secreting cell and the subject to be treated. Typically, a plurality of differences will be present in both Class I and Class II antigens will be present, and these differences will be recognizable either in an antibody-mediated tissue typing cytotoxicity test, or a mixed lymphocyte reaction between the cytokine-secreting cells and lymphocytes from the subject to be treated. Differences in Class I antigens are generally more relevant, since most cell types do not express Class II. In certain embodiments of this invention, the number of MHC differences is irrelevant, as long as the cells are allogeneic. In other embodiments of this invention, MHC differences, particularly Class I differences are preferred as a potentiating factor in immune stimulation. In this context, at least 2 differences are preferred; at least about 3 differences are even more preferred. When using human cells, differences are especially preferred in the HLA-A -B and -C loci.

The cell will also generally be a cell that can be maintained in culture for a large number of replications and genetically desired, if necessary. Typically, the cell will be a neoplastic cell, a malignantly transformed cell, or the progeny of such cells. Cells may be deliberately transformed into long-lived cell lines by any method, including, but not limited to, fusion with other cell lines, treatment with a chemical carcinogen, or infection with a suitable virus such as Epstein-Barr virus or oncogenic virus. More usually, the cell will be the progeny of a primary tumor occurring in the appropriate species, that has been established in ex vivo culture.

In certain embodiments of this invention, tumor cells are used as the allogeneic cytokine-expressing cell, wherein the tumor is a different type from that of the subject being treated. This may provide additional bystander effect by providing a plurality of novel immunogenic antigens. In this context, the tumor cell is preferably selected so as to comprise a large proportion or particularly high level of an immunogenic epitope. In other embodiments of this invention, tumor cells are used from a tumor type similar or identical to that of the subject in terms of its tissue source, morphological characteristics, surface antigen expression, clinical manifestations, and any other relevant criteria. This is preferred when it is desirable to increase the probability that a tumor-associated antigen, or a plurality of such antigens may be overexpressed both on the cytokine-expressing tumor cell of the vaccine, and tumor cells in the subject being treated. Shared tumor-associated antigens may permit cis stimulation of therapeutically relevant immune reactivity.

Cells may be stimulated to secrete cytokines at suitable levels according to any method known in the art, including, but not limited to, coculturing with other cells or treatment of the cells with the same or different cytokines.

Most typically, in order to provide a high and reliable level of cytokine expression, the cells are genetically altered so as to synthesize the cytokine at an elevated level. It is recognized that certain cells such as lymphocytes and macrophages may already produce detectable levels of certain cytokines. "Elevated levels" of expression that occur as a result of genetic alteration exceed levels observed in cells not genetically altered or otherwise manipulated in the same way, but that are otherwise similar.

Genetic alteration may be effected by any method known in the art. Typically, an encoding sequence for the desired cytokine is operatively linked to a heterologous promoter that will be constitutively or inducibly active in the target cell, along with other controlling elements and a poly-A sequence necessary for transcription and translation of the protein. The expression cassette thus composed is introduced into the cell by any method known in the art, such as calcium-phosphate precipitation, insertion using cationic liposomes, or using a viral vector tropic for the cells. Methods of genetic alteration are described in the patent publications cited in relation to some of the cytokines listed earlier.

One preferred method is the use of adenovirus vectors. For example see, Graf et al. (1995) Soc. Neuroscience 21:838.5. Briefly, adenoviral recombinant expression vectors prepared by genetic engineering of commercially available plasmids such as those supplied by Microbix, Canada. Suitable infection conditions and multiplicities of infection (MOI) may be determined in preliminary experiments using a reporter gene such as β-galactosidase, and then used for cytokine transfer (Kammersheidt et al.). An advantage of using a viral vector is that the vector may first be replicated, and then an entire population of cells may be infected and altered. Accordingly, genetically altered cytokine secreting cells may be established as a cell line, or a freshly obtained cell isolate or cell culture is altered de novo just prior to use in a vaccine of this invention. In the latter instance, preparation of the vaccine would additionally comprise the step of transducing a population of cells allogeneic to the intended recipient with a vector comprising an encoding region for a particular cytokine of interest. Transduction using adenoviral vectors and the like is especially preferred when it is desirable to achieve very high levels of cytokine expression by the genetically altered cells.

An even more preferred preferred method of genetic alteration is the use of a retroviral vector comprising a suitable expression cassette. Non-limiting illustrations are provided in the example section below, and may also be found in Santin 1995b, 1995c & 1996. Although this approach may not achieve quite the same level of expression available in some other systems, a particular benefit is that the genetically altered cell is highly stable in the amount of cytokine produced. This means that the level of expression can be characterized exactly, and relied upon as a reagent composition through multiple passages and different storage conditions. In addition, genetically altered cells may be prepared which are capable of producing cytokine even after inactivation by irradiation. The levels of cytokine can be adjusted upwards, where necessary, simply by increasing the number of genetically altered cells in the dosage.

As shown in Examples 1-4, tumor lines can be created using the LXSN retroviral vector that produce cytokine at a stable and reliable level through multiple cell divisions. Levels of cytokine secretion may be determined by immunoassay or bioassay. Cells with these properties are generally preferred, since they can be biochemically characterized and clinically tested in advance. Accordingly, it is generally preferable to clone genetically-altered cells and select high-producer clones. Supernatant of $1 \times 10^6$ cells/ml cultured in 10 ml medium for 48 hours at 37° C. may contain the following preferred levels of cytokines: IL-4, IL-2, TNF-$\alpha$, the secreted form of M-CSF, or most other cytokines of about the same molecular mass are preferably produced at least 500, more preferably at least about 1000, even more preferably at least about 2000 pg/mL. GM-CSF is preferably produced at least 100, more preferably at least about 200, even more preferably at least about 400 pg/mL. Membrane-associated cytokines, where the majority produced by the cell, should be biosynthesized at a rate preferably 25%, more preferably 50%, and even more preferably 100% of the range obtained for high-level producers of the secreted form.

It is also highly desirable that a substantial proportion of cytokine-producing cells remain viable and be able to secrete the cytokine of interest after inactivation to prevent proliferation. Preferred treatments halt development of at least about 95%, or more preferably at least about 99% of the cells. Typically, when using irradiation, the levels required are 2,500 rads, more preferably 5,000 rads, even more preferably 10,000 rads, and still more preferably 20,000 rads. The cells preferably produce cytokine 2 days after irradiation at a rate that is at least about 10%, more preferably at least about 20%, more preferably at least about 50%, still more preferably at least about 100% of the pre-irradiated level, when standardized for viable cell number.

The cytokine producing cells can also be modified in other ways, if desired. In particular, they can be genetically altered to express additional proteins, including but not limited to additional cytokines, additional tumor-associated antigens, or additional cell-surface markers, such as adhesion molecules like ICAM-1, histocompatibility antigens, or costimulation markers like the B-cell marker B7-1 or B7-2. Alternatively or in addition, they may be modified so as to produce multiple copies of the same or similar proteins, including multiple copies of the same cytokine in membrane-associated or secreted form, or both. Transduction for expression of multiple proteins or multiple protein copies may be conducted concurrently or sequentially. More than one genetic alteration may be viewed as optional, and is not required for the practice of this invention.

Assembly of the vaccine: The vaccines of this invention comprise autologous tumor cells (or an alternative source of tumor-associated antigen) and at least one cell allogeneic to the host that produces a cytokine of therapeutic importance.

As described earlier, certain embodiments of this invention comprise a plurality of different allogeneic cells, each of which produces a different cytokine. Preferably, the cytokines produced by each different cell are amongst those listed herein.

In one method, cell components of the vaccine are prepared and combined in bulk at the desired ratio(s) to provide sufficient cells for the entire course of treatment envisioned. The mixture is stored frozen, and aliquots are thawed seriatim for each administration. This ensures a consistency amongst the cell ratio.

To allow adjustments to components of the vaccine or the ratios used, it is generally preferable to assemble the vaccine close to the time of administration. Various cell populations may be collected in advance, and cultured or cryopreserved as necessary to ensure sufficient numbers of cells for administration and testing throughout the planned protocol.

It is important to remove any additional components used in preparing the cells which may have an unwanted effect in the subject. In particular, fetal calf serum, bovine serum components, or other biological supplements in the culture medium are typically removed so as to avoid an immunological side reaction against them. Typically, the cell components of the vaccine are washed, such as by repeated gentle centrifugation, into a suitable pharmacologically compatible excipient. Compatible excipients include isotonic saline, with or without a physiologically compatible buffer like phosphate or Hepes and nutrients such as dextrose, physiologically compatible ions, or amino acids, and various culture media suitable for use with lymphocyte populations, particularly those devoid of other immunogenic components. Carrying reagents, such as albumin and blood plasma fractions and nonactive thickening agents, may also be used. Non-active biological components, to the extent that they are present in the pharmacological preparation, are preferably derived from the same species, and are even more preferably obtained previously from the subject to be treated.

The vaccine compositions of this invention may optionally include additional active components working independently or in concert with the tumor associated antigen and activated allogeneic cells. Such optional components include but are not limited to isolated or recombinant cytokines, particularly those explicitly referred to in this disclosure, adjuvants, and other cell types. Preferred additional components are bacillus of the *M. bovis* strain Calmette-Guerin (BCG) or extracts thereof, or alternatively, the A60 mycobacterial antigen complex (Maes et al.).

A vaccine composition of this invention is deemed "suitable" for administration to a human if reasonable and acceptable standards have been taken to ensure that the vaccine itself will not confer additional major pathology on the recipient. Side effects such as local inflammation, induration, or pain, or a febrile response may be unavoidable and are generally acceptable if the treatment is otherwise successful in a substantial proportion of patients. However, the composition should be reasonably free of: a) unrelated and pathological infectious or chemical agents, particularly from the donor of the allogeneic lymphocytes; b) undesirable growths as may be generated or propagated in tissue culture, such as bacteria or bacterial toxins, mycobacteria, and viruses; c) unacceptable levels of oncogenic agents or aggressively growing cancer cells not originating from the subject being treated; and d) components liable to initiate or effect an undesirable immune reaction, particularly anaphylactic shock. Particular tests that can be used are listed in the example section of this disclosure.

The compositions of the present invention, and subcomponents thereof may be supplied in unit dosage or kit form. Kits of this invention can comprise various components of a cellular vaccine or pharmaceutical composition therefor provided in separate containers. The containers may separately contain cells or antigens such that when mixed together constitute a vaccine of this invention in unit dosage or multiple dosage form. Preferred kits comprise in separate containers: cytokine-secreting allogeneic cells; and tumor-associated antigen from the human, particularly primary tumor cells from the human, or progeny thereof. Alternatively, the kits may comprise a cell or cell mixture in one container and a pharmaceutical excipient in another container. Preferred kits of this nature comprise cytokine-secreting allogeneic cells in one container, and an excipient in another. The user can employ the excipient to prepare their own tumor antigen or autologous tumor cells, said preparation then being combined with the cytokine-secreting cells for administration to a subject. Packaged compositions and kits of this invention typically include instructions for storage, preparation and administration of the composition.

Use of Cellular Vaccines in Cancer Treatment

The compositions of this invention may be administered to subjects, especially but not limited to human subjects. They are particularly useful for eliciting an immune response against a tumor-associated antigen, or for treating cancer.

Objectives of treatment: One purpose of administering the vaccine is to elicit an immune response. The immune response may include either humoral or cellular components, or both. Humoral immunity may be determined by a standard immunoassay for antibody levels in a serum sample from the treated individual.

Since cellular immunity is thought to play an important role in immune surveillance of cancer, generating a cellular immune response is frequently a particular objective of treatment. As used herein, a "cellular immune response" is a response that involves T cells, and can be observed in vitro or in vivo.

A general cellular immune response may be measured as the T cell proliferative activity in cells particularly PBL) sampled from the subject after vaccine administration. Inactivated tumor cells, preferably derived from the subject, are used as stimulators. A non-specific mitogen such as PHA serves as a positive control; incubation with an unrelated stimulator cell serves as a negative control. After incubation of the PBMCs with the stimulators for an appropriate period (typically 5 days), [$^3$H]thymidine incorporation is measured. If desired, determination of the subset of T cells that is proliferating can be performed using flow cytometry. T cell cytotoxicity (CTL) can also be measured. In this test, an enriched T cell population from the subject are used as effectors in a standard $^{51}$Cr release assay. Tumor cells are radiolabeled as targets with about 200 μCi of Na$_2^{51}$CrO$_4$ for 60 minutes at 37° C., followed by washing. T cells and target cells (~1×10$^4$/well) are then combined at various effector-to-target ratios in 96-well, U-bottom plates. The plates are centrifuged at 100×g for 5 minutes to initiate cell contact, and are incubated for 4-16 hours at 37° C. with 5% CO$_2$. Release of $^{51}$Cr is determined in the supernatant, and compared with targets incubated in the absence of T cells (negative control) or with 0.1% TRITON™ X-100 (positive control).

Another purpose of administering the vaccine is for treatment of a neoplastic disease, particularly cancer. Beneficial effect of the vaccine will generally be at least in part immune mediated, although an immune response need not be positively demonstrated in order for the compositions and treatment methods to fall within the scope of this invention, unless otherwise required.

Suitable subjects: The compositions of this invention may be used for administration to both human and non-human vertebrates. They provide advantages over previously available compositions particularly in outbred populations, and particularly in spontaneous tumors. Veterinary applications are contemplated within the scope of the invention.

Cellular vaccines are designed for use in human subjects, and are especially suitable for human treatment. The vaccines may be given to any human subject with the discretion of the managing physician. Typically, the subject will either have cancer, or be at substantial risk of developing cancer.

Typical human subjects for therapy comprise two groups, which may be distinguished by clinical criteria. Patients with "advanced disease" or "high tumor burden" are those who bear a clinically measurable tumor. A clinically measurable tumor is one that can be detected on the basis of tumor mass (e.g., by palpation, MRI, CAT scan, X-ray, or radioscintigraphy; positive biochemical or histopathological markers on their own are insufficient to identify this population).

A vaccine composition embodied in this invention is administered to patients with advanced disease with the objective of palliating their condition. Ideally, reduction in tumor mass occurs as a result, but any clinical improvement constitutes a benefit. Clinical improvement includes decreased risk or rate of progression or reduction in pathological consequences of the tenor.

A second group of suitable subjects is known in the art as the "adjuvant group". These are individuals who have had a history of cancer, but have been responsive to another mode of therapy. The prior therapy may have included (but is not restricted to) surgical resection, radiotherapy, traditional chemotherapy, and other modes of immunotherapy. As a result, these individuals have no clinically measurable tumor by the definition given above. However, they are suspected of being at risk for recurrence or progression of the disease, either near the original tumor site, or by metastases. The adjuvant group may be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes.

A vaccine composition embodied in this invention is administered to patients in the adjuvant group in order to elicit an anti-cancer response primarily as a prophylactic measure against recurrence. Ideally, the composition delays recurrence of the cancer, or more preferably, reduces the risk of recurrence (i.e., improves the cure rate). Such parameters may be determined in comparison with other patient populations and other modes of therapy.

Of course, crossovers between these two patient groups occur, and the vaccine compositions of this invention may be administered at any time that is appropriate. For example, therapy may be conducted before or during traditional therapy of a patient with high tumor burden, and continued after the tumor becomes clinically undetectable. Therapy may be continued in a patient who initially fell in the adjuvant group, but is showing signs of recurrence.

Examples of tumors that can be treated by the compositions and methods of this invention include the following: pancreatic tumors, such as pancreatic ductal adenocarinomas; lung tumors, such as small and large cell adenocarcinomas, squamous cell carcinoma, and brionchoalveolar carcinoma; colon tumors, such as epithelial adenocarcinoma and their metastases; and liver tumors, such as hepatoma and cholangiocarcinoma. Also included are breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional squamous cell carcinoma; tumors of the RES system, such as nodular or diffuse B or T cell lymphoma, plasmacytoma, and acute or chronic leukemia; skin tumors, such as malignant melanoma; and soft tissue tumors, such as soft tissue sarcoma and leiomyosarcoma. Of especial interest are brain tumor, such as astrocytoma, oligodendroglioma, ependymoma, medulloblastomas, and primitive neural ectodermal tumor. Included in this category are gliomas, glioblastomas, and gliosarcomas. Also of especial interest is ovarian carcinoma.

The immune status of the individual may be any of the following: The individual may be immunologically naive with respect to certain tumor-associated antigens present in the composition, in which case the compositions may be given to initiate or promote the maturation of an anti-tumor response. The individual may not be currently expressing anti-tumor immunity, but can have immunological memory, particularly T cell memory relating to a tumor-associated antigen comprised in the vaccine, in which case the compositions can be given to stimulate a memory response. The individual can also have active immunity (either humoral or cellular immunity, or both) to a tumor-associated antigen comprised in the vaccine, in which case the compositions may be given to maintain, boost, or maturate the response, or recruit other arms of the immune system. The subject should be at least partly immunocompetent, so as to minimize a graft versus host reaction of pathological scope. However, it is recognized that cancer patients often show a degree of immunosuppression, and this does not necessarily prevent the use of the compositions of the invention, as long as the compositions may be given safely and effectively. Immunocompetence in the subject may be of host origin, or may be provided by way of a concurrent adoptive transfer treatment.

Modes of administration and dose: The compositions of this invention may be administered to the subject at any site, particularly a site that is "distal" to or "distant" from the primary tumor.

The route of administration of a pharmaceutical composition may be parenteral, intramuscular, subcutaneous, intradermal, intraperitoneal, intranasal, intravenous (including via an indwelling catheter), via an afferent lymph vessel, or by another route that is suitable in view of the tumor being treated and the subject's condition. Because of low-level inflammation or induration that may occur for the few days after administration, relatively non-invasive methods are preferred, particularly subcutaneous routes.

The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^5$ to $10^{10}$ cells, including allogeneic cytokine-producing cells, and autologous tumor cells or an equivalent thereof. Where a tumor antigen preparation or tumor cell extract is used in place of autologous tumor cells, the amount of tumor antigen present should be equivalent to what would be provided in the level of cells indicated. The number of autologous tumor cells may be adjusted to accommodate unusually high or low levels of tumor antigen expression. Where a plurality of allogeneic cells genetically altered to produce different cytokines is used, the range referred to includes the total number of such cells. The number of allogeneic cytokine-producing cells is adjusted according to the level of cytokines produced by the cell population.

Preferably, between about $10^6$ to $10^9$ of allogeneic cytokine-producing cells and about $10^6$ to $10^9$ autologous tumor cells are used; more preferably between about $2\times10^6$ and $5\times10^8$ cells in each cell population is used; more preferably between about $5\times10^6$ and $2\times10^8$ cells in each population are used; even more preferably between about $1\times10^7$ and $1\times10^8$ cells in each population are used. Multiple doses, when used in combination to achieve a desired effect, each fall within the definition of an effective amount.

The various components of the cellular vaccine are present in an "effective combination", which means that there are sufficient amounts of each of the components for the vaccine to be effective. This will depend not only on the absolute number of cells, but also on the ratio of the various components of the vaccine one to another. Preferred ratios of total allogeneic cytokine-secreting cells to autologous tumor cells or equivalent are 100:1 to 1:100, more typically they are between about 25:1 and 1:25, even more preferably they are between about 10:1 and 1:10, still more preferably they are between about 3:1 and 1:3. Often more important than the actual number of cytokine-producing cells used is the biosynthetic capability of the cells; fewer cells being required where the biosynthetic capability is higher. Preferably, the allogeneic cells in a dose of the vaccine are capable of synthesizing at least about 0.1 ng, more preferably at least about 0.5 ng, more preferably at least about 2 ng, even more preferably at least about 10 ng of the cytokine of interest during a 1 hour incubation under physiological conditions. Where a plurality of different cytokine-producing cells are used, ratios are chosen to give appropriate levels of biological activity; typically between 25:1 and 1:25, more usually between 5:1 and 1:5 on a molar basis. Determination of optimal cell dosage and ratios is a matter of routine determination, as described in the example section below, and within the skill of a practitioner of ordinary skill, in light of the instructions provided herein.

For embodiments of the invention where the vaccine consists essentially of cells autologous to the patient expressing a membrane cytokine, the number of cells is between $10^5$ and $10^{10}$ per dose; more preferably between about $4\times10^6$ and $1\times10^9$ cells per dose; more preferably between about $1\times10^7$ and $4\times10^8$ cells per dose even more preferably between about $2\times10^7$ and $2\times10^8$ cells per dose. Multiple doses, when used in combination to achieve a desired effect, each fall within the definition of an effective amount.

The pharmaceutical compositions of this invention may be given following, preceding, in lieu of, or in combination with, other therapies relating to generating an immune response or treating cancer in the subject. For example, the subject may previously or concurrently be treated by chemotherapy, radiation therapy, and other forms of immunotherapy and adoptive transfer. Example 7 describes the use of a vaccine of this invention in combination with such chemotherapeutic agents as Cisplatin, combination Cisplatin/Cyclophaphamide, Cisplatin/Cyclophosphamide/Doxorobicin or Taxol. Where such modalities are used, they are preferably employed in a way or at a time that does not interfere with the immunogenicity of the compositions of this invention. The subject may also have been administered another vaccine or other composition in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

In a particular embodiment, the subject will have previously been treated with an intra-tumor implant of stimulated allogeneic lymphocytes, such as is described in International Patent Application WO 96/29394. Combination protocols wherein another mode of vaccination or other therapy preceding or following administration of an autologous tumor cell/allogeneic cytokine-secreting cell vaccine, are embodied in the present invention.

Timing of administration is within the judgment of the managing physician, and depends on the clinical condition of the patient, the objectives of treatment, and concurrent therapies also being administered. At an appropriate time in patient management, an initiating dose is given, and the patient is monitored for either an immunological or clinical response, often both. Suitable means of immunological monitoring include a one-way MLR using patient's PBL as responders and primary tumor cells as stimulators. An immunological reaction may also be manifest by a delayed inflammatory response at the injection site. Suitable means of monitoring the tumor are selected depending on the tumor type and characteristics, and may include magnetic resonance imaging (MRI), radioscintigraphy with a suitable imaging agent, monitoring of circulating tumor marker antigens, and the subject's clinical response. An example of an appropriate clinical marker is serum CA-125 for the monitoring of advanced ovarian cancer. Hempling et al. (1993) *J. Surg. Oncol.* 54:38-44. Additional doses may be given as appropriate, typically on a monthly, semimonthly, or preferably a weekly basis, until the desired effect is achieved. Thereafter, and particularly when the immunological or clinical benefit appears to subside, additional booster or maintenance doses may be given as required.

When multiple doses of a cellular vaccine are given to the same patient, some attention should be paid to the possibility that the allogeneic lymphocytes in the vaccine may generate an anti-allotype response. The use of a mixture of allogeneic cells from a plurality of donors, and the use of different allogeneic cell populations in each dose, are both strategies that can help minimize the occurrence of an anti-allotype response.

During the course of therapy, the subject is evaluated on a regular basis for side effects at the injection site, or general side effects such as a febrile response. Side effects are managed with appropriate supportive clinical care.

Cell Lines

This invention includes the cell lines listed in the Table below. These cell lines are provided and described for the convenience of the practitioner, and may be used, inter alia, for the preparation of certain vaccines of this invention, or for methods of treatment of this invention. None of the cell lines listed is required for the general practice of the invention, except in particular embodiments where a cell line is explicitly required.

TABLE 1

| Designation | Origin | Description | ATCC Accession No. |
| --- | --- | --- | --- |
| UCI-107E IL-4 GS | Ovarian carcinoma cell line UCI-107 | genetically altered to express IL-4 | |
| UCI-107M GM-CSF-MPS | | genetically altered to express GM-CSF | |
| UCI-107A IL-2 AS | | genetically altered to express IL-2 | |
| ACBT | Glioblastoma cell line | parental cell line | |
| ACBT/TNF-G | | genetically altered to express TNF-α | |
| ACBT/IL-4-T | | genetically altered to express IL-4 | |
| ACBT/IL-2-C2 | | genetically altered to express IL-2 | |
| ACBT/GM-CSF-M4 | | genetically altered to express GM-CSF | |

Upon allowance and issuance of this application as a United States Patent, all restriction on the availability of the deposits will be irrevocably removed, and access to the designated deposits will be available during pendency of the above-named application to one determined by the Commissioner to be entitled thereto, under 37 CFR § 1.14 and 35 USC § 1.22. Moreover, the designated deposits will be maintained for a period of thirty (30) years from the date of deposit, or from five (5) years after the last request for the deposit; or for the enforceable life of the U.S. patent, whichever is longer.

The examples presented below are provided as a further guide to a practitioner of ordinary skill in the art, and are not meant to be limiting in any way.

EXAMPLES

Example 1

An Ovarian Cancer Cell Line Transduced to Express IL-4

A human ovarian cancer cell line was genetically altered to secrete IL-4, using a retroviral vector comprising an IL-4 encoding construct. The cell line was stable, and capable of IL-4 biosynthesis even after an inactivating dose of radiation. The cell line expressed MHC Class I and Her-2/neu antigens, but no MHC Class II antigens, ICAM-1, CA-125, or IL-4 receptors.

The human ovarian cell line UCI-107 was established from a previously untreated patient with a primary Stage III serous papillary adenocarcinoma of the ovary. The UCI-101 and UCI-107 cell lines have been previously characterized (Gamboa-Vujicic et al. Submitted, Gynecol. Oncol.) and were kindly provided by Dr. Alberto Manetta (University of California, Irvine Medical Center). Cells were maintained at 37° C., 5% $CO_2$ in complete media (CM) containing RPMI 1640 (Gibco Life Technologies), 10 percent fetal bovine serum (FBS, Gemini Bioproducts, Calabassas, Calif.), and 1 percent penicillin/streptomycin sulfate (Irvine Scientific, Santa Ana, Calif.).

Retroviral vectors were constructed as follows: The pLXSN plasmid was kindly provided by Dr. A. Dusty Miller (Fred Hutchinson Cancer Center, Seattle, Wash.). This plasmid, derived from a Maloney murine leukemia virus (MMLV) contains the neophosphotransferase gene whose constitutive expression is driven by the SV40 enhancer/promoter, the 5' retroviral LTR of the integrated vector drives the expression of an inserted gene. The human IL-4 cDNA was obtained from ATCC in the Okayama and Berg pCD cloning vector, and was excised using BamHI restriction enzyme. Okayama et al. (1983) *Mol. Cell Biol.* 3:228-289. The cDNA was then cloned into the BamHI restriction site in the multiple cloning region of pLSXN. Proper orientation of the cDNA was determined by diagnostic restriction endonuclease digests. Once constructed, retroviral plasmid DNA was then purified by CsCl gradient density centrifugation.

Purified retroviral plasmid DNA (LXSN/IL-4) was used to transduce the murine esotropic packaging cell line GP-E86 by the calcium phosphate method. Forty-eight-hour supernatant from these cells was then used to infect the murine amphotropic-packaging cell line, PA317. The PA-317-packaging cell line was obtained from the ATCC and maintained in CM. Transduced PA317 cells were selected by resistance to G418. Isolated clones were expanded, aliquoted, and frozen under liquid nitrogen in a master cell bank. The supernatant from a transduced PA317 clone, containing infectious, replication-incompetent retrovirus, was used to infect the human carcinoma cell lines. Briefly, human ovarian carcinoma cell lines were seeded in 100-mm tissue culture dishes at densities of $1\times10^6$ cells in 10 ml CM and incubated for 4 hr at 37° C., 5% $CO_2$ to allow adherence. After incubation, the medium was aspirated and replaced with 5 ml of 2% polybrene in phosphate-buffered saline (PBS), (Aldrich Chemical Co. Inc., Milwaukee, Wis.). After 30 min at 37° C., 5% $CO_2$, 10 ml of retroviral supernatant was added, and retroviral-mediated gene transfer was accomplished by overnight incubation. Supernatants were then aspirated and replaced with CM. After an additional 48-hr incubation in CM at 37° C., 5% $CO_2$, selection of transduced clones was accomplished by culture in CM containing 0.075% G418 (geneticin, Gibco Life Technologies). Clones were isolated after 14 days using sterile 8×8 8-mm cloning cylinders (Belco Glass, Inc., Vineland, N.J.) and expanded for 3 weeks in CM containing G418. Parent cell lines were used as positive controls for G418 resistance. After clonal selection in G418, transduced cell lines were returned to CM for expansion and study.

Cells were established in CM at a density of $0.5\times10^6$ cells/10 ml in 100 mm tissue culture dishes. Cell counts were conducted every 12, 24, 48, 72 and 96 hours, and the number of viable cells was determined using trypan blue exclusion. Experiments were conducted to compare the growth of non-transduced (parental) and transduced tumor cell lines and to evaluate the level of cytokine production over time. Supernatants were collected and frozen at −20° C. (for subsequent ELISA evaluation of cytokine levels) and culture dishes trypsinized to determine cell count and viability.

Parental, IL-4 transductants, and vector control cells, were seeded in 100 mm tissue culture dishes (Corning) at a density of $1\times10^6$ cells/ml in 10 ml CM. After 48 hour incubation at 37° C., 5 percent $CO_2$, supernatant was aspirated, rendered cell-free by centrifugation at 1,500 rpm for 10 minutes, then stored at −20° C. IL-4 concentration was then determined by ELISA, employing a commercially available kit (Research & Diagnostic Systems, Minneapolis, Minn.). Table 2 shows the level of secretion of Interleukin-4 from clones of genetically altered human serous papillary ovarian cancer cells

TABLE 2

| Designation | IL-4 pg/mL |
|---|---|
| Transduced UCI-101 clones | |
| A | 140 |
| B | (not detectable) |
| C | 49 |
| D | 40 |
| E | 87 |
| G | 93 |
| H | 38 |
| I | 93 |
| L | 42 |
| M | 32 |
| N | (not detectable) |
| O | (not detectable) |
| Average | 51.1 |
| Transduced UCI-107 clones | |
| A | 32 |
| B | 83 |
| C | 90 |
| D | 35 |
| E | 1300 |
| F | 30 |
| G | 80 |
| H | 513 |
| L | 170 |
| M | 297 |
| N | 265 |
| P | 330 |
| Q | 615 |
| X | 79 |
| Y | 68 |
| Average | 265.8 |

As expected, each parental line and cells transduced with vector alone did not produce detectable levels of IL-4. The best IL-4 producing clone, termed UCI 107E IL-4 GS, was expanded and employed to form a master cell bank for further testing and extensive characterization.

The parental cell line UCI 107 has the characteristic morphology of ovarian epithelial cells grown in vitro. The morphology of UCI 107 cells transduced with the LXSN vector alone or LXSN containing the IL-4 gene was indistinguishable from that of parental 107 cells. The doubling time of parental, vector control, and UCI 107E IL-4 GS cells was determined to be 15.3, 15.7, and 18.6 hr, respectively.

Figure 1:
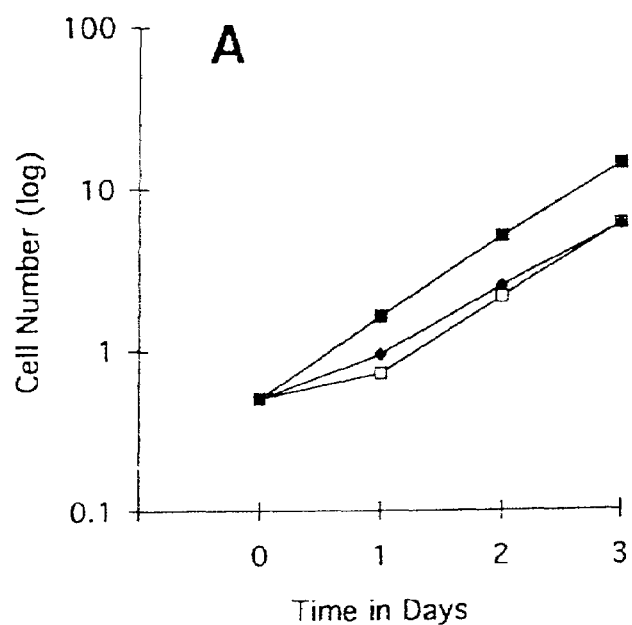
Figure 1:
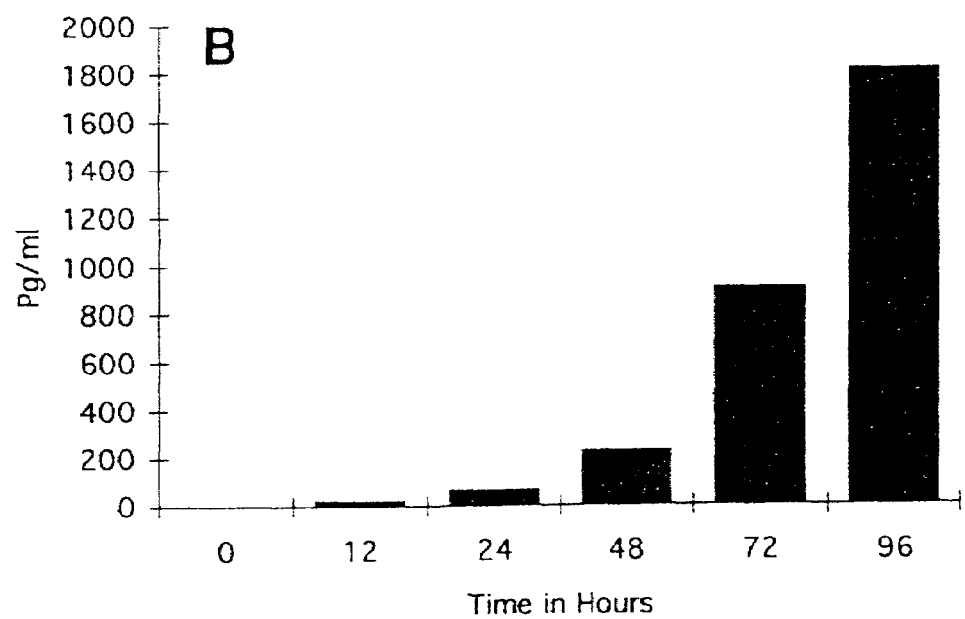

FIG. 1 shows the growth and IL-4 secretion by UCI 107E IL-4 GS cells. No changes in the growth rate of these cells have been observed in vitro over 35 passages and 6 months of culture. Levels of IL-4 production were consistently in the range of 900 to 1300 pg/ml/$10^5$ cells/48 hr during the 6 months of passage. Extensive tests performed on the UCI 107E IL-4 GS master cell bank (MCB) revealed that this line is free of the presence of mycoplasma, bacteria, and infectious viruses.

Southern analysis was conducted using the $Neo^R$ gene to probe the UCI 107E IL-4 and the parental UCI 107 line. Briefly, concentrated suspensions of tissue culture cells were lysed in TNE buffer (10 mM Tris, 100 mM NaCl, 1 mM EDTA, pH 7.5) containing 0.5% SDS, treated with 50 μg/ml proteinase K overnight at 37° C., then extracted with phenol and chloroform. The DNA solution was precipitated in 100% ethanol, spooled out and resuspended in 10 mM Tris, 0.1 mM EDTA (pH 8). Ten μg of high molecular weight DNA was digested with SstI (GIBCO/BRL, Grand Island, N.Y.), separated by electrophoresis on a 0.8% agarose gel and transferred to Gene Screen Plus (Dupont NEN, Boston, Mass.). Transfer, hybridization, and washing were performed according to manufacturer's specifications. Random primer IL-4 probe was prepared by the method of Tabor and Struhl (1988) In Current Protocols in Mol. Biol. vol. 1:pp 2.2.1-2.2.3. The results confirmed that after 20 passages, UCI 107E IL-4 still contained the vector DNA.

Stability of IL-4 secretion to irradiation was tested as follows: Cells were irradiated in a 15 ml conical tube in CM at room temperature with gamma rays (Cesium 137) at a dose rate of 200 rads/minute. Immediately after irradiation, cells were seeded in a Petri dish culture plate at a density of $1 \times 10^6$ cells in 10 ml of CM. Test doses of 1,000 to 10,000 rads were applied. Irradiated cells were cultured at 37° C. in a 5% $CO_2$ atmosphere and the medium was completely changed every four days in all the dishes. Every 48 hours, culture supernatants were collected from the dish for cytokine production and the number of viable cells was assessed by light microscopy by trypan blue exclusion.

Figure 2A:
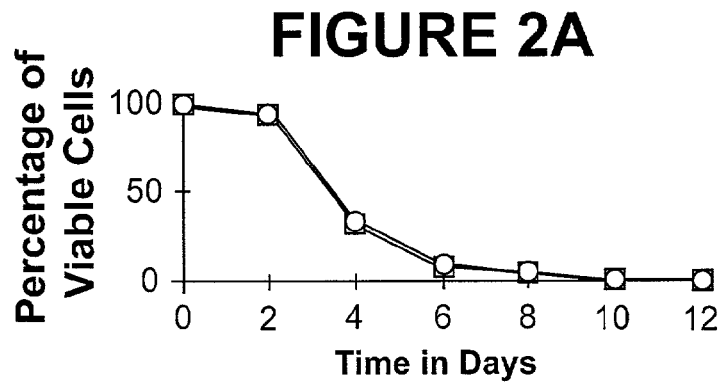
Figure 2B:
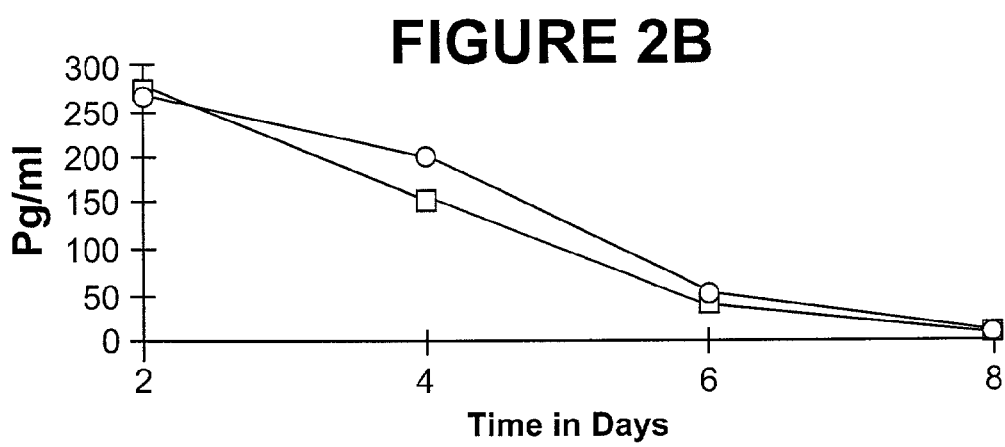
Figure 2C:
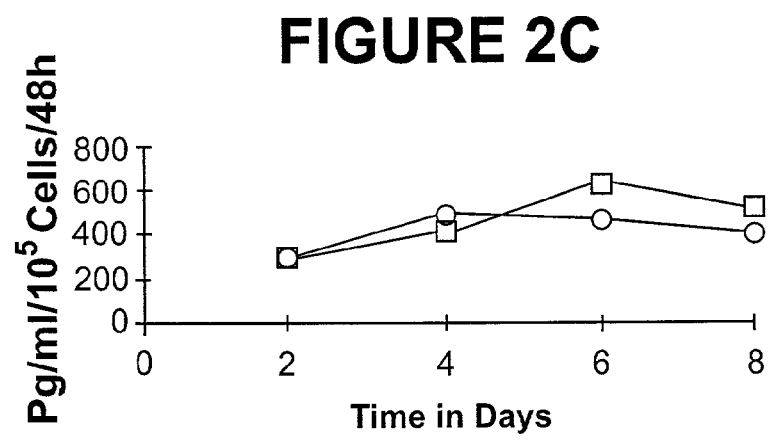

Results of this experiment are shown in FIGS. 2A-C. Cells irradiated with between 2,500 and 10,000 rads remained viable for about 8 days but all the cells were dead by 3 weeks. Cells irradiated with 1,000 rads recuperated and continued to proliferate. Levels of cytokine production were detectable for 8 days at all doses and closely paralleled the number of viable cells. FIG. 2B shows IL-4 production after irradiation at 5,000 rads (□) or 10,000 rads (■) in three separate experiments. FIG. 2C shows IL-4 production standardized in pg/ml/$10^5$ cells/48 hr by UCI 107E IL-4 GS cells after irradiation at 5,000 or 10,000 rads in two separate experiments. No statistically significant differences in survival were seen among cells irradiated with 2,500, 5,000, and 10,000 rads on days 2 ($p=0.72$), 4 ($p=0.14$), 6 (p '0.10), and 8 ($p=0.3$).

Proteins of the major histocompatibility complex, adhesion molecules, and tumor-associated antigens such as CA-125 are important for both recognition and destruction of tumor cells by the immune system. Accordingly, expression of representative antigens was examined by fluorescence-activated cell sorting (FACS). Monolayers of parental cells, vector controls, and IL-4 transduced cells were harvested with 0.1% trypsin and 0.2% EDTA. Harvested cells were fluorescently labeled using the following primary antibodies: anti-HLA class I and anti-HLA class II (monoclonal antibodies (mAb) W6/32 and CR3-43, respectively; Accurate Chemical and Scientific Corp.), anti-ICAM-1 (mAb LB-2; Becton-Dickinson); anti-CA-125 (mAb OC125; Signet Laboratories); anti-HER-2/new p185 (mAb TA-1; Oncogene Science), and anti-IL-4-receptor (Genzyme Diagnostic).

Figure 3A:
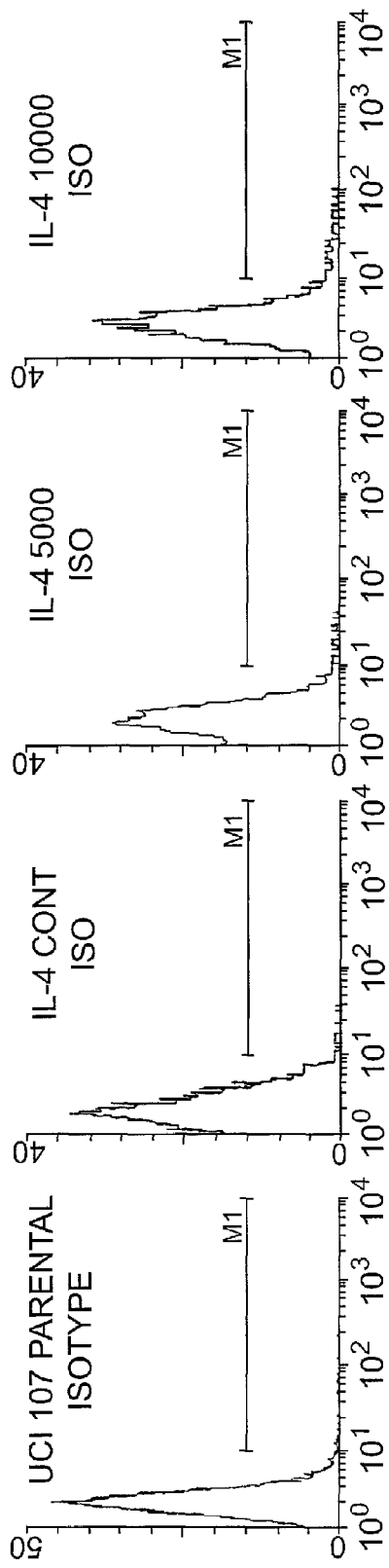
Figure 3B:
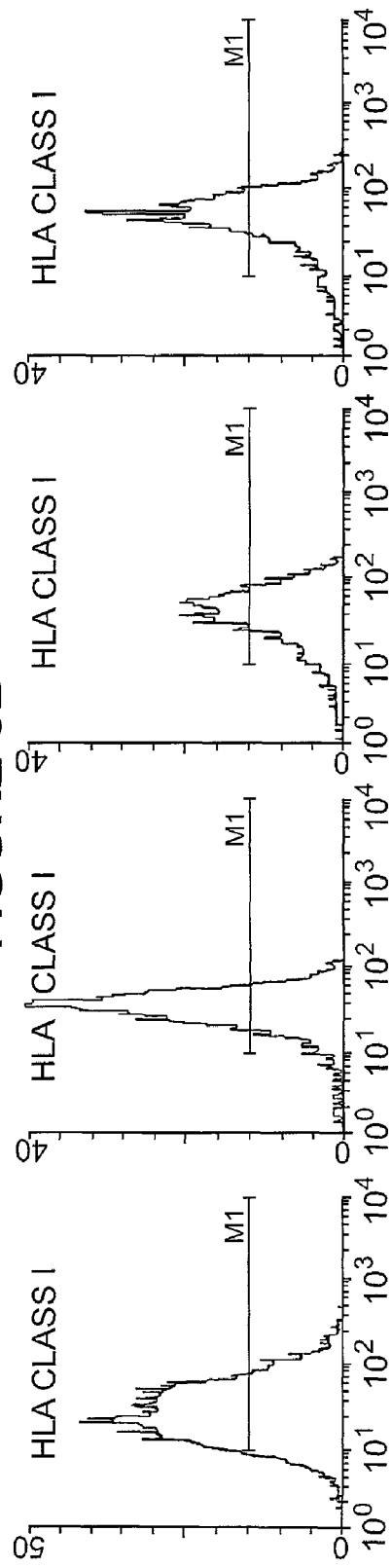
Figure 3C:
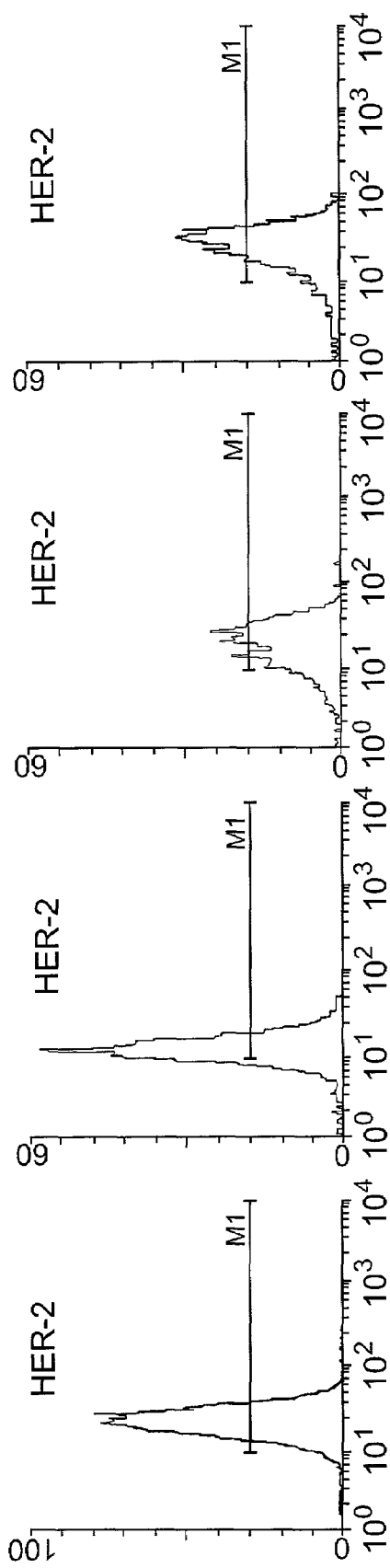

The expression of surface antigens detected by FACS analysis is illustrated in FIGS. 3A-C. Parental cells, vector controls, and 107E IL-4 GS cells constitutively express MHC class I antigens and Her-2/neu, but did not express MHC class II antigens, CA-125, ICAM-1, or IL-4 receptors. Expression of surface antigens was also determined at 2 or 8 days after irradiation. MHC class I antigen and Her-2/new antigen expression increased significantly at all radiation doses, and tended towards higher expression at higher doses. Irradiation did not induce expression of HLA class II antigens, ICAM-I, or CA-125.

Collectively, these results indicate that UCI 107E IL-4 GS cells constitute a stable IL-4 secreting cell line. The cells can be irradiated to stop replication effectively, yet maintain IL-4 production for up to a week.

Example 2

An Ovarian Cancer Cell Line Transduced to Express GM-CSF

A human ovarian carcinoma cell line (UCI-107) was genetically engineered to secrete human cytokine granulocyte-macrophage colony stimulating factor (GM-CSF), similar to the method described in Example 1. One clone, termed UCI-107M GM-CSF-MPS, constitutively secretes high levels of GM-CSF (~500 pg/ml/$10^5$ cells 48 hours) UCI-107M GM-CSF-MPS cells express MHC Class I and Her2/New surface antigens, but do not express detectable MHC Class II, ICAM-1 or the tumor-associated antigen CA-125. After a radiation dose of 10,000 rads, GM-CSF secretion continued until about Day 8.

The choice of transducing an ovarian carcinoma cell line with the GM-CSF gene has been made in light of the important role of GM-CSF in the maturation and function of specialized antigen-presenting cells. GM-CSF is one of the most potent stimulators of systemic anti-tumor immunity.

The pLXSN plasmid is described in Example 1. The human GM-CSF cDNA was obtained from the ATCC in the Okayama and Berg pCD cloning vector, and was excised using BamHI restriction enzyme. The cDNA was then cloned into the BamHI restriction site in the multiple cloning region of pLSXN. Proper orientation of the cDNA was determined by diagnostic restriction endonuclease digests. Once constructed, retroviral plasmid DNA was then purified by CsCl gradient density centrifugation.

Purified retroviral plasmid DNA (LXSN/GM-CSF) was used to transfect the murine esotropic packaging cell line GP-E86 as before. Forty-eight hour supernatant from these cells was then used to infect the murine amphotropic packaging cell line PA317, and selected by resistance to G418. The supernatant from a transduced PA317 clone, containing infectious, replication incompetent retrovirus, was used to infect the UCI-107 cell line. After clonal selection in G418, transduced cell lines were returned to CM for expansion and study.

Parental, GM-CSF transductants and vector control cells, were seeded in 100 mm tissue culture dishes (Corning) at a density of $1 \times 10^6$ cells/ml in 10 ml CM. After 48 h incubation at 37° C., 5% $CO_2$, supernatant was aspirated, centrifuged at 1,500 rpm for 10 minutes, then stored at −20° C. GM-CSF concentration was determined by ELISA, employing a commercially available kit (Research & Diagnostic Systems, Minneapolis, Minn.). The biologic activity of GM-CSF was measured in a cell proliferation assay using a GM-CSF factor-dependent human cell line, TF-1, provided by Dr. Monica Tsang (Research and Diagnostic Systems). The level of biologic activity correlated with the level of GM-CSF detected by ELISA.

Cultures of each transduced LXSN-GM-CSF clone and LXSN vector control were established for 48 h, and the media tested for the presence of GM-CSF. As expected, parental UCI-107 cells and cells transduced with the LXSN vector alone did not produce detectable levels of GM-CSF.

TABLE 3

| Transduced UCI-107 clones | |
|---|---|
| Designation | GM-CSF pg/mL |
| A | 55 |
| A1 | 15 |

TABLE 3-continued

Transduced UCI-107 clones

| Designation | GM-CSF pg/mL |
|---|---|
| B | 25 |
| B1 | 98 |
| C | 9 |
| C1 | 7 |
| D | 83 |
| D1 | 73 |
| E | 7 |
| E1 | 61 |
| F | 5 |
| F1 | 21 |
| G | 47 |
| G1 | 39 |
| H | 13 |
| H1 | 134 |
| I | 86 |
| I1 | 12 |
| L | 126 |
| L1 | 149 |
| M | 420 |
| M1 | 67 |
| N | 31 |
| N1 | 63 |
| O | 79 |
| O1 | 115 |
| P | 31 |
| Q | 49 |
| R | 35 |
| S | not detectable |
| T | 74 |
| U | 34 |
| V | not detectable |
| X | 8 |
| Y | 146 |
| Z | 22 |

Of 36 clones originally selected, the highest GM-CSF producing clone, termed UCI-107M GM-CSF-MPS, was expanded and employed to form a master cell bank for further testing and extensive characterization:

The parental cell line UCI 107 has the characteristic morphology of ovarian epithelial cells grown in vitro. The morphology of UCI 107 cells transduced with the LXSN vector alone or LXSN containing the GM-CSF gene was indistinguishable from that of parental 107 cells. The doubling time of the parental, vector control and UCI-107M GM-CSF-MPS cells was approximately 20 to 26 h.

Over a period of 6 months and a total of 35 passages, levels of GM-CSF production by UCI-107M GM-CSF-MPS were consistently in the range of 420 to 585 pg/ml/$10^5$ cells/48 hours. The GM-CSF secreting clone was evaluated for successful gene insertion by Southern hybridization after 20 passages of the cells, and the presence of the inserted gene was confirmed.

To determine the stability of GM-CSF secretion after irradiation, UCI-107M GM-CSF-MPS cells were irradiated and supernatants from individual subcultures were evaluated for cytokine production. No effects on cell growth were observed at doses of less than 1,000 rads. At higher doses, approximately 90% of the cells were viable 48 h after irradiation, with 30% and 10% viability at 4 and 6 days, respectively. All cells were dead after three weeks. No statistically significant differences in survival were seen among cells irradiated with 2,500, 5,000 or 10,000 rads. Secretion of GM-CSF continued until about day 8, suggesting a decrease but not a complete inhibition in the biosynthesis and release of the cytokine in cells surviving irradiation.

The expression of membrane antigens was examined by FACS analysis on parental, LXSN vector control and UCI-107M GM-CSF-MPS cells. All three cells constitutively express MHC Class I antigens (parental cells: 87.5%, non-fluorescence index (MFI)=33.6; GM-CSF secreting cells: 92-9%, MFI=53.9); Her-2/neu, (95.8%, MFI=20.8; and 93.3%, MFI=22.1% respectively), but did not express MHC Class II determinants, CA-125 or ICAM-1. The production of GM-CSF or the presence of the LXSN vector had no detectable effect on the expression of these antigens. Increased expression of MHC Class I and Her-2/neu surface antigens was observed in irradiated cells compared with the non-irradiated controls. Gamma irradiation did not induce neo-expression of antigens not originally expressed on the parental cells; in particular, HLA Class II antigens, ICAM-I or CA-125.

Example 3

An Ovarian Cancer Cell Line Transduced to Express IL-2

A human ovarian carcinoma cell line (UCI-107) was genetically engineered to secrete the cytokine Interleukin-2 (IL-2), by retroviral mediated gene transduction similar to the method outlined in Example 1. This line was transduced with the LXSN retroviral vector containing the human IL-2 gene and the neomycin resistance selection marker. One clone termed UCI-107A IL-2 AS, was shown to constitutively secrete high levels of IL-2 (i.e., 2,000 to 2,300 pg/ml/$10^5$ cells/48 hours) for over 35 passages and six months of study. Unlike parental and vector transduced cells (both of which were diploid), UCI-107A Il-2 AS failed to express MHC Class I and Her2/Neu surface antigens. In addition, UCI-107A IL-2 AS cells exhibited a distinct in vitro morphology, and were resistant to gamma irradiation.

The human IL-2 cDNA was obtained from ATCC in the Okayama and Berg pCD cloning vector and was excised using BamHI restriction enzyme. The cDNA was then cloned into the BamHI restriction site in the multiple cloning region of the pLSXN plasmid. Proper orientation of the cDNA was determined by diagnostic restriction endonuclease digests. Retroviral plasmid DNA was purified by CsCl gradient density centrifugation.

The purified retroviral plasmid DNA (LXSN/IL-2) was used to transfect the murine esotropic packaging cell line GP-E86 by the calcium phosphate method. Forty-eight hour supernatant from these cells was then used to infect the murine amphotropic packaging cell line, PA317 obtained from ATCC, and selected by resistance to Geneticin. UCI-107 cells were seeded into 100 mm tissue culture dishes at densities of $1 \times 10^6$ cells in 10 ml CM. 10 ml of retroviral supernatant was added, and incubated with the cells overnight. Clones were isolated after 14 days and expanded for three weeks in CM containing G418.

IL-2 concentration in clone supernatants was determined by ELISA, employing a commercially available kit (Research & Diagnostic Systems, Minneapolis, Minn.). The biologic activity of IL-2 was measured in a cell proliferation assay using an IL-2 dependent murine cytotoxic cell line, CTLL-2 provided by Dr. Monica Tsang (Research and Diagnostic Systems). The level of biologic activity correlated with the level of IL-2 detected by ELISA.

As expected, parental UCI-107 cells and cells transduced with the LXSN vector alone did not produce detectable levels of IL-2. Of 13 clones selected, the highest IL-2 producer, termed UCI-107A IL-2 AS, was shown to have a level of IL-2 production consistently in the range of 2,000 to 2,300 pg/ml/$10^5$ cells/48 hours during the six months of the observation period. This clone was expanded and employed to form a master cell bank for further testing and characterization.

The morphology of UCI-107 cells transduced with the LXSN vector was indistinguishable from that of parental UCI-107 cells. In contrast, UCI-107 cells containing the IL-2 gene exhibited significantly altered morphology, being much more spindle-shaped than parental cells. The doubling time of parental, vector control and UCI-107A IL-2AS cells was approximately 20 to 26 hours, stable for over 35 passages and 6 months of culture.

The IL-2 secreting clone transduced with LXSN-IL-2 and selected in G418 was evaluated for successful gene insertion by Southern hybridization probing for the $Neo^R$ gene confirmed the presence of the retroviral vector in the genome of the transduced UCI-107 cells.

In irradiation tests, no effects on cell growth were observed at doses of less than 5,000 rads. At doses of 10,000 rads, approximately 90 percent of the cells were viable 48 hours after irradiation, 45 percent after 4 days and 10 percent after 6 days. All the cells were dead after three weeks. IL-2 production was maintained at high levels for about 6 days, after which cytokine secretion rapidly decreased parallel with the viable cell number.

Parental UCI-107 cells and vector control cells express MHC Class I antigens, 87.5% and 94.8% respectively; Her-2/neu, 95.8% and 94.3% respectively; but did not express MHC Class II determinants, CA 125 or ICAM-1. In contrast, UCI-107A IL-2 AS cells did not display any of these antigens at detectable levels.

Seven and eight, 7 week-old female BALB/C nude mice, respectively, were injected i.p. with $10 \times 10^6$ LXSN vector control or UCI-107A IL-2 AS cells, and the animals were followed for eight weeks to evaluate tumor formation. Vector control cells formed large solid tumor nodules within 3 weeks after injection, and all the animals died within 25 days. In contrast, seven of eight nude mice injected with UCI-107A IL-2 AS cells remained alive and tumor-free after eight weeks.

Susceptibility of tumors to lysis by freshly isolated PBL from normal donors was tested in 4- and 18-hour $^{51}Cr$ release cytotoxicity assays and long-term cytotoxicity assays (Finke et al.). Cytotoxic activity was observed against UCI-107 parental and vector control cells at four hours. In contrast, the UCI-107A IL-2 AS cells were killed only after 18 h or longer:

TABLE 4

| Target Cell Employed | Effector to Target Ratio (E:T) | 4 hr $^{51}Cr$ Release Assay | 18 hr $^{51}Cr$ Release Assay | 72 hr Long Term Killing Assay |
|---|---|---|---|---|
| UCI 107 PARENTAL | 25:1 | 28.0 ± 1.1* | 42.3 ± 2 | 44.5 ± 2.5 |
|  | 10:1 | 2.0 ± 1.6 | 13.7 ± 3.1 | 11.0 ± 0 |
|  | 5:1 | 2.7 ± 1.2 | 2.7 ± 1.2 | 9.0 ± 2.0 |
|  | 2.5:1 | 0 ± 0 | 0 ± 0 | not done |
| UCI 107 LXSN (vector control) | 25:1 | 29.9 ± 2.0 | 42.7 ± 0.9 | 48.5 ± 5.5 |
|  | 10:1 | 6.2 ± 1.0 | 10.8 ± 6.7 | 18.0 ± 6.5 |
|  | 5:1 | 2.5 ± 0.6 | 1.6 ± 1.6 | 13.0 ± 6.0 |
|  | 2.5:1 | 0 ± 0 | 0 ± 0 | not done |
| UCI 107A IL-2 AS | 25:1 | 0 ± 0 | 54.4 ± 10.4 | 76.0 ± 0 |
|  | 10:1 | 0 ± 0 | 28.4 ± 1.6 | 75.0 ± 0 |
|  | 5:1 | 0 ± 0 | 2.4 ± 2.4 | 69.5 ± 0.5 |
|  | 2.5:1 | 0 ± 0 | 0 ± 0 | not done |

*Mean ± SD

The resistance of the UCI-107A IL-2 AS cell to cytotoxic killing in these in vitro assays may provide an advantage to the use of these cells in vaccine compositions. The lack of expression of MHC Class I, Class II and ICAM-1 antigens may reduce the anti-allogeneic response that would ordinarily eliminate cells of the vaccine.

Example 4

Cytokine-expressing Human Glioblastoma Cells

In this example, human glioblastoma cells were genetically altered to secrete TNF-α, IL-2, IL-4, or GM-CSF. The engineered cell lines were characterized for potential use in vaccine trials.

A human glioblastoma cell line designated ACBT was established as follows: Tumor tissue was obtained at the time of surgery from a 42 year old male patient with recurrent glioblastoma multiforma of the right temporal lobe. Tumor tissue was minced into 20 mm pieces and digested overnight in collagenase (Sigma Chemical Co., N.J.). The cell suspension was then filtered through a sterile 100 μm nylon mesh (Tetro Inc.), and washed 3 times in RPMI 1640 (GIBCO Life Technologies, Grand Island, N.Y.), 10% fetal bovine serum (FBS; GIBCO Life Technologies) and 1% penicillin/streptomycin. Cells cultured from the original tissue were confirmed to be glioblastoma in origin as determined by GFAP positively and morphology.

The cDNA gene for human TNF-α was obtained from the ATCC. It was cloned into the HpaI restriction site in the multiple cloning region of plasmid pLNCX (Example 1) by a double blunt end ligation to generate the recombinant plasmid pLNCT. Proper sense orientation of the TNF cDNA was confirmed by analytical restriction enzyme digests. The expression of TNF-α in the LNCT vector is controlled by the internal immediate early enhancer/promoter of the cytomegalovirus, and the expression of the neomycin resistance gene is under control of the 5' Long Terminal Repeat (LTR) of the integrated retroviral vector.

The IL-2, IL-4 and GM-CSF cDNA containing vectors were constructed in a similar fashion. The cDNA for each of these cytokines was obtained from ATCC and was cloned into the BamHI restriction site in the multiple cloning region of plasmid pLXSN to generate the recombinant plasmids pLXSN/IL-2, pLXSN/IL-4, and pLXSN/GM-CSF. Cytokine expression in this vector system is controlled by the 5' LTR of the integrated proviral vector, and expression of the neomycin resistance gene is under control of the SV40 early promoter.

Infectious TNF gene containing retroviral particles were generated by transfecting the amphotropic packaging cell line PA317 with purified pLNCT DNA, or with pLNCX DNA (the vector control). In brief, the procedure comprised combining 10 μg of CsCl purified plasmid of pLNCT DNA with 10 μg calf thymus DNA. The DNA mixture was used to transfect $1 \times 10^6$ PA317 cells, which were seeded 4 hours prior in a 100 mm tissue culture dish, by the calcium phosphate precipitation method. After a 48-hour incubation period, the media was removed from the transfected cells and centrifuged at 3,000×g for 5 minutes to remove cellular debris. The resulting supernatant contained infectious retroviral particles (vLNCT) and was used to transduce ACBT cells. The transfection process comprised plating $1\times10^4$, $1\times10^5$, $10\times10^6$ and $2\times10^6$ ACBT cells in 10 ml of media in 100-mm tissue culture dishes at 37° C. in a 5% $CO_2$ incubator to allow for cells to adhere. After incubation, the media was replaced with 5 ml of polybrene (20 μg/ml in phosphate buffered saline, pH 7.4, PBS), and incubated for hour at 37° C. The polybrene was removed, and the PA317 viral containing supernatant was added to the ACBT glioblastoma cells. After 24 hours, the viral supernatant was replaced by 10 ml. of selection media containing G418 (733 μg/ml active G418) at a concentration of 600 μg/ml. Individual colonies of G418 resistant ACBT/TNF-α clones were isolated after 14 days using sterile 8×8 mm glass cloning rings, and expanded in CM containing G418 for several weeks. The transfected cell lines were then returned to CM for maintenance and expansion to create vector control clones of which ACBT/LNCS was isolated and used as a vector control cell line.

Gene transfer using the IL-2, IL-4 and GM-CSF containing vectors were conducted in similar fashion to that of TNF-α. Recombinant DNA plasmid containing these cytokine genes were used first to transfect the esotropic packaging cell line GP|E-86. After a 48 hour incubation period, the media was removed and centrifuged at 3,000×g for 5 minutes. The viral particle containing supernatant was then used to infect the amphotropic packaging cell line PA317. Afterwards, individual PA317 clones were selected by their ability to grow in culture media containing G418. The supernatants from individual PA317 clones secreting infectious LXSN/IL-2, LXSN/IL-4 or LXSN/GM-CSF viral particles were used to transduce ACBT glioblastoma cells in a similar fashion to the LNCT transfection as described above.

TNF secretion was determined by ELISA using a polyclonal antibody against recombinant human TNF. IL-2, IL-4 and GM-CSF secretion by each of the respective transduced ACBT clones were determined by ELISA, employing commercially available kits. Results are shown in Tables 5 and 6:

TABLE 5

|  | TNF pg/ml | IL-2 pg/ml | IL-4 pg/ml | GM-CSF pg/ml |
| --- | --- | --- | --- | --- |
| ACBT parental line | 24 | 212 | 12 | 22 |
| LNCX (vector control for TNF) | 24 | — | — | — |
| LXSN (vector control for IL-2, IL-4, & GM-CSF) | — | 28 | 12 | 16 |

TABLE 6

| ACBT/TNF | | ACBT/IL-2 | | ACBT/IL-4 | | ACBT/GM-CSF | |
| --- | --- | --- | --- | --- | --- | --- | --- |
| Designation | TNF (pg/ml) | Designation | IL-2 (pg/ml) | Designation | IL-4 (pg/ml) | Designation | GM-CSF (pg/ml) |
| D | 2,394 | C1 | 1,319 | P | 2,373 | M1 | 205 |
| F | 2,265 | C2 | 2,420 | T | 2,865 | M3 | 274 |
| G | 2,569 | C3 | 102 |  |  | M4 | 550 |
| K | 2,288 | C4 | 720 |  |  | M5 | 52 |
| M | 836 | C5 | 163 |  |  | M6 | 294 |
|  |  | C6 | 2,066 |  |  | M7 | 76 |
|  |  | C7 | 1,255 |  |  | M8 | 373 |
|  |  | C8 | 198 |  |  | M10 | 253 |
|  |  | C9 | 38 |  |  | M11 | 25 |
|  |  |  |  |  |  | M12 | 65 |

The ACBT/parental and vector control cells produced minimal to low levels of each of the respective cytokines. Clones ACBT/TNF-G, ACBT/IL-2-C2, ACBT/IL-4-T and ACBT/GM-CSF-M4 produced the highest levels of the indicated cytokine and were used for analysis of growth characteristics and kinetics of cytokine secretion.

The parental cell line, ACBT, has a characteristic morphology of spindle shaped astrocytoma cells grown in vitro. The ACBT cells transduced with pLXSN or pLNCS vectors alone, or with the vectors containing the cytokine genes, exhibited morphologies similar to that of the parental cell. The growth rates of parental, LNCS vector control, LXSN vector control, ACBT/IL-2-C2, ACBT/IL-4-T and ACBT/GM-CSF-M4 cells were similar, with doubling times ranging from 25 to 35 hours. The ACBT/TNF-G cell line had a somewhat slower growth rate of 41 hours.

Figure 4:
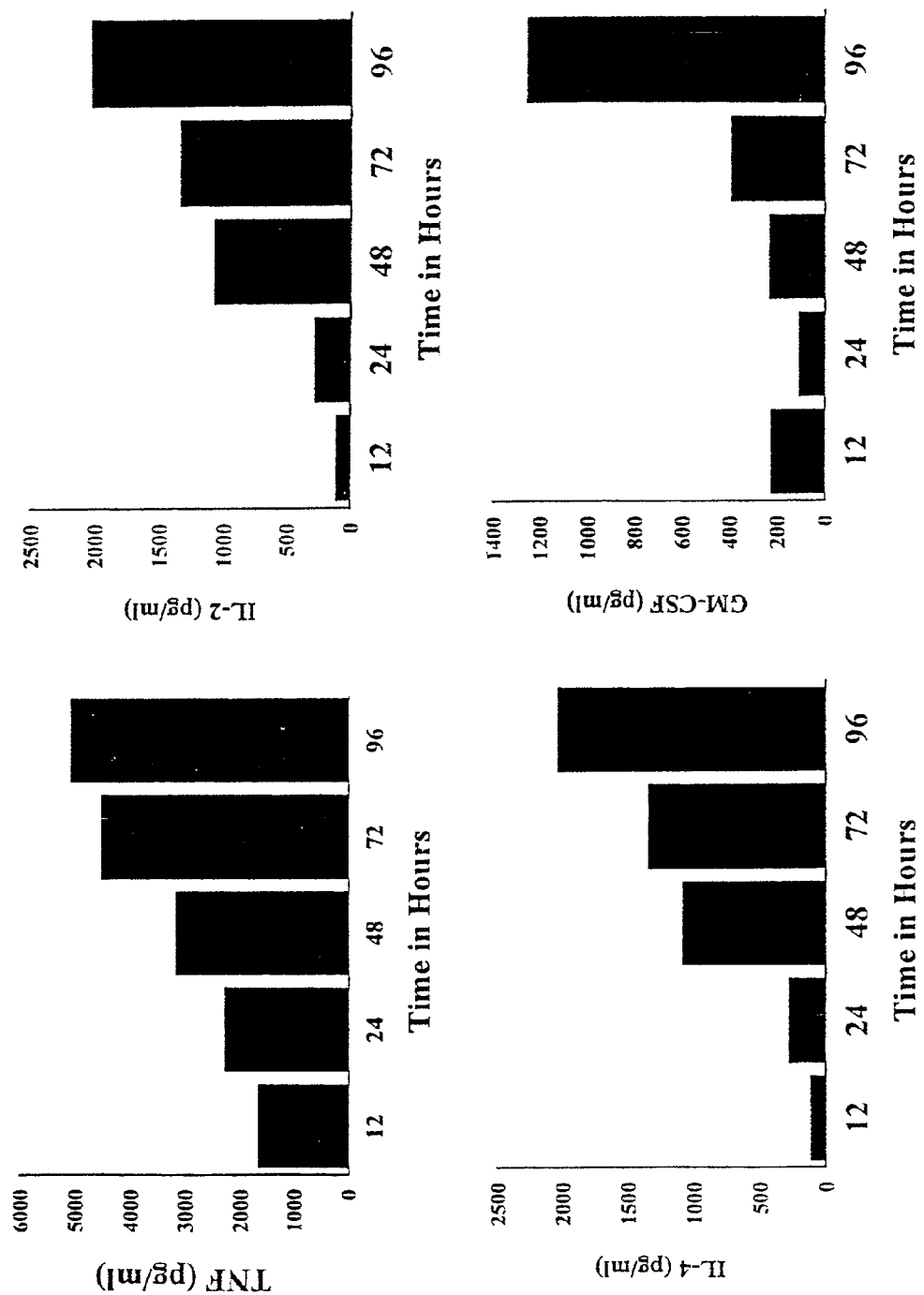
FIG. 4 is a four-panel graph depicting cytokine secretion by human glioblastoma clones genetically altered to express TNF-α, IL-4, IL-2, or GM-CSF.

FIG. 4 shows cytokine production by $0.5\times10^6$ cells/10 ml over a period of 96 hours. Upper left, clone ACBT/TNF-G; lower left, clone ACBT/IL-4-T; upper right, clone ACBT/IL-2-C2; lower right, clone ACBT/GM-CSF-M4. Cytokine production increases steadily over time as a result of cell replication. The best TNF-producing clone, ACBT/TNF-G, was expanded to form a master cell bank for further testing and extensive characterization. TNF production was studied over a period of 2.5 months and 15 passages, and was consistently in the range of 2500 to 3500 pg/ml.

Southern blot analysis of DNA from the ACBT/TNF-G cell line confirms that the TNF-α encoding vector is integrated into the genome of the host cell.

Figure 5:
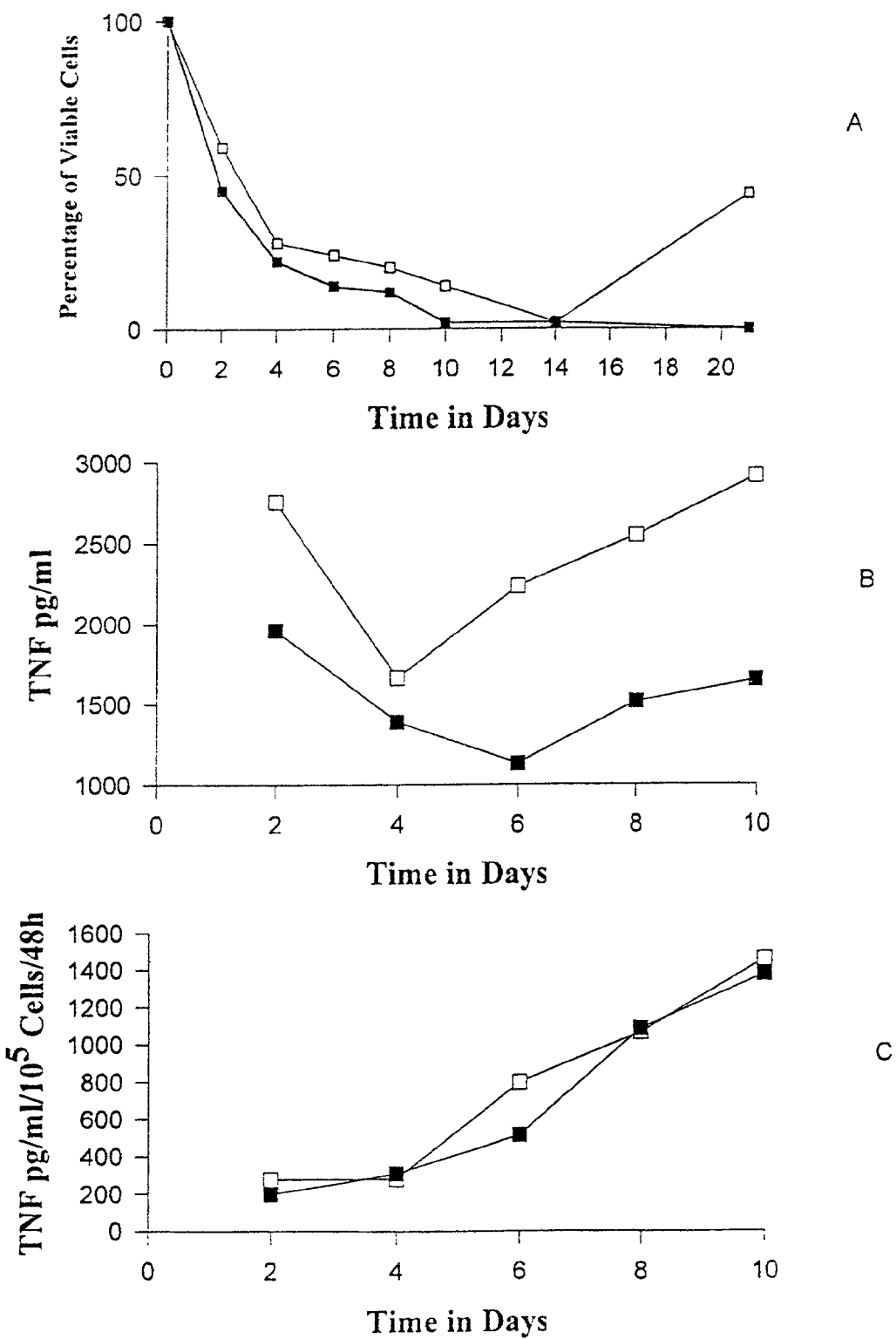
FIG. 5 is a three-panel graph showing the effects of irradiation on viability and TNF-α secretion by the glioblastoma cell line ACBT/TNF-G at 10,000 (□) or 20,000 (■) rads.

ACBT/TNF-G cells were given either 10,000 (□) or 20,000 (■) rads of γ-irradiation from a cesium source, and then were established as monolayer cultures in CM (FIG. 5). 59% and 45% of the cells were viable 48 hours after irradiation with 10,000 and 20,000 rads, respectively; and only 2% of cells were viable 14 days later in each group. At 3 weeks, all of the cells that had received 20,000 rads were dead. Some cells that had received 10,000 rads survived, and replicated to 44% of the original cell number plated (Panel A). TNF production in the culture initially decreased after irradiation, but then steadily increased up to day 10 (Panel B). TNF production expressed per $10^5$ viable cells steadily increased over time after irradiation. There was no observable difference in the levels of cytokine secretion per $10^5$ viable cells between the treatment groups.

The expression of MHC antigens was analyzed by FACS on parental, vector control and ACBT/TNF-G cells. The results obtained are summarized in Table 7.

TABLE 7

| Cells | Isotype | | MHC Class I | | MHC Class II | | CD54 (ICAM-I) | |
|---|---|---|---|---|---|---|---|---|
| | MCF | % pos | MCF | % pos | MCF | % pos | MCF | % pos |
| ACBT parental cells | 147.6 | (6.9%) | 859.9 | (62.6%) | 136.0 | (5.7%) | 277.6 | (39.6) |
| ACBT LNCX vector control | 84.1 | (3.3%) | 606.3 | (50.8%) | 156.6 | (3.3%) | 239.4 | (28.9%) |
| ACBT/TNF-G transduced unirradiated | 24.3 | (5.1%) | 643.9 | (99.9%) | 22.5 | (4.4%) | 225.9 | (97.5%) |
| ACBT/TNF-G 2 d after 10,000 rads | 40.9 | (8.4%) | 878.1 | (99.9%) | 34.7 | (5.0%) | 392.5 | (97.8%) |
| ACBT/TNF-G 2 d after 20,000 rads | 34.4 | (4.9%) | 828.2 | (99.9%) | 36.6 | (4.8%) | 327.9 | (97.9%) |

Parental, LNCX vector control and ACBT/TNF-G cells and expressed MHC Class I and CD54 (ICAM-1) surface antigens. The mean channel fluorescence (MCF) of cells expressing these antigens were similar for the parental, vector control and ACBT/TNF-G cell lines. However, the percent positive cells (shown in parentheses) was greater for the TNF-producing clone. ACBT parental cells did not express Class II antigens, and transduction with the TNF gene did not cause neo-expression of Class II antigens.

γ-irradiation mildly upregulated the expression of both Class I and ICAM-1 surface antigens on ACBT/TNF-G cells at both 10,000 and 20,000 rads with increases in the MCF. γ-irradiation did not, however, cause neo-expression of Class II molecules on the transduced cell line.

The ACBT/TNF-G cell line was extensively tested for the presence of various microorganisms by our own and outside laboratories. The results revealed that the ACBT/TNF-G cell line is free of mycoplasma, bacteria, the DNA viruses Epstein-Barr, human hepatitis B, human cytomegalovirus, and replication competent retroviruses.

Example 5

Membrane M-CSF Expression IN A Syngeneic Vaccine Model

Expression of the M-CSF gene results in two different isoforms of the M-CSF protein due to alternative post-transcriptional splicing within exon 6. One form of the protein is secreted as a 45 kd homodimeric glycoprotein, and the other form remains associated with the cell membrane. Stein et al. (1991) *Oncogene* 6:601. The secreted form (sM-CSF) induces proliferation and differentiation of monocyte progenitors, is responsible for the stimulation of the effector functions of macrophages such as cytokine production and enhanced tumoricidal activity, and may function as a chemoattractant for circulating monocytes. In the brain, sM-CSF is believed to induce proliferation and activation of microbial cells. Alterman et al. (1994) *Alt. Chem. Neurpathol.* 21:177. The membrane bound isoform (mM-CSF) has also been shown to be biologically functional in that it is capable of stimulating macrophage colony formation of bone marrow stem cells. Stein et al. (1990) *Blood* 76:1308, T9 glioblostoma cells expressing the mM-CSF isoform, but not the secreted form, are killed in vitro by tumoricidal macrophages.

In this example, the therapeutic value of the two M-CSF isoforms was investigated in glioma destruction by using T9 glioblastoma cells genetically modified to express either the soluble or the membrane-associated isoforms of M-CSF in a syngeneic Fischer rat brain tumor model.

T9 glioblastoma tumor cells (induced by the repeated intravenous injection of N-nitrosomethylurea in a Fischer F344 rat; Benda et al. (1971) *J. Neurosurg.* 34:310 were provided by Dr. J. Yoshida, Department of Neurosurgery, Nagoya University, Japan. An intracranial (i.c.) injection of $1 \times 10^5$ T9 cells into the Fischer rat brain is 100% lethal in 20-days. 9L gliosarcoma cells (induced by repeated i.v. injection of N-nitrosomethylurea; Albright et al.) were obtained from Dr. Carol Kruse, University of Colorado Health Science Center, Denver, Colo. $10^6$ 9L cells implanted into the brain of Fischer F344 rats is lethal in 18-28 days. The MADB106 mammary adenocarcinoma cell line (induced by i.v. injection of 9,10-dimethyl-1,2-benzanthracene in a Fischer F344 rat) was obtained from Dr. Craig Reynolds of the National Cancer Institute, Frederick, Md. MADB106 cells develop lethal tumors when implanted s.c. or i.c. in Fischer 344 rats.

T9 glioblastoma cells were transduced with a retroviral expression vector (LXSN) containing the human cDNA gene for the secreted or membrane-associated isoform of M-CSF (obtained from M. R. Jadus). As determined by ELISA, clone T9/sM-CSF(H1) secretes M-CSF at a level of 2000 pg/ml when $1 \times 10^6$ cells are cultured in 10 ml of media for 3 days. Secreted M-CSF was shown to be biologically active by its ability to induce macrophage colonies from rodent bone marrow samples. Flow cytometric analysis indicated that clone T9/mM-CSF(C2) expressed a high level of M-CSF on its cell surface, whereas T9/sM-CSF, vector control and parental T9 cells did not. Clone T9/mM-CSF (C2) was effectively killed by macrophages in an in vitro co-culture experiment but T9/sM-CSF(HI) and parental T9 glioblastoma cells were not. Clone T9/mM-CSF(C2) and T9/sM-CSF(H1) did not differ in their in vitro growth rate, the expression of MHC class I or class II antigens, expression of ICAM-1 (CD54), or morphology, in comparison with T9 parental or T9/LXSN vector control cells.

Tumor implantation studies were conducted as follows: Animals were anesthetized by an intramuscular injection of ketamine (87 mg/kg) and xylazine (6.5 mg/kg). A hand-held Dremel drill was used to create a shallow depression 3 mm to the right of the sagittal suture and 1 mm posterior to the coronal suture. 10 μl tumor cell suspension in PBS was injected into the posterior parietal lobe of the brain at a depth of 4 mm using a Hamilton syringe, and the needle track was sealed with melted paraffin.

Animals were implanted intracranially (i.c.) with $1 \times 10^5$ T9/mM-CSF or T9/sM-CSF cells. It was found that animals injected with T9/sM-CSF have only a slightly longer survival compared to controls implanted with T9 parental cells. In contrast, 80% of the animals implanted with T9/mM-CSF cells survived. Rejection of mM-CSF cells amongst various clones correlated with the level of membrane expression of M-CSF. Clone C2 expressed the highest level of M-CSF on its membrane and showed 73% overall rejection, whereas clone F12 showed a much lower level of expression and was rejected in only 20% of animals.

Figure 6:
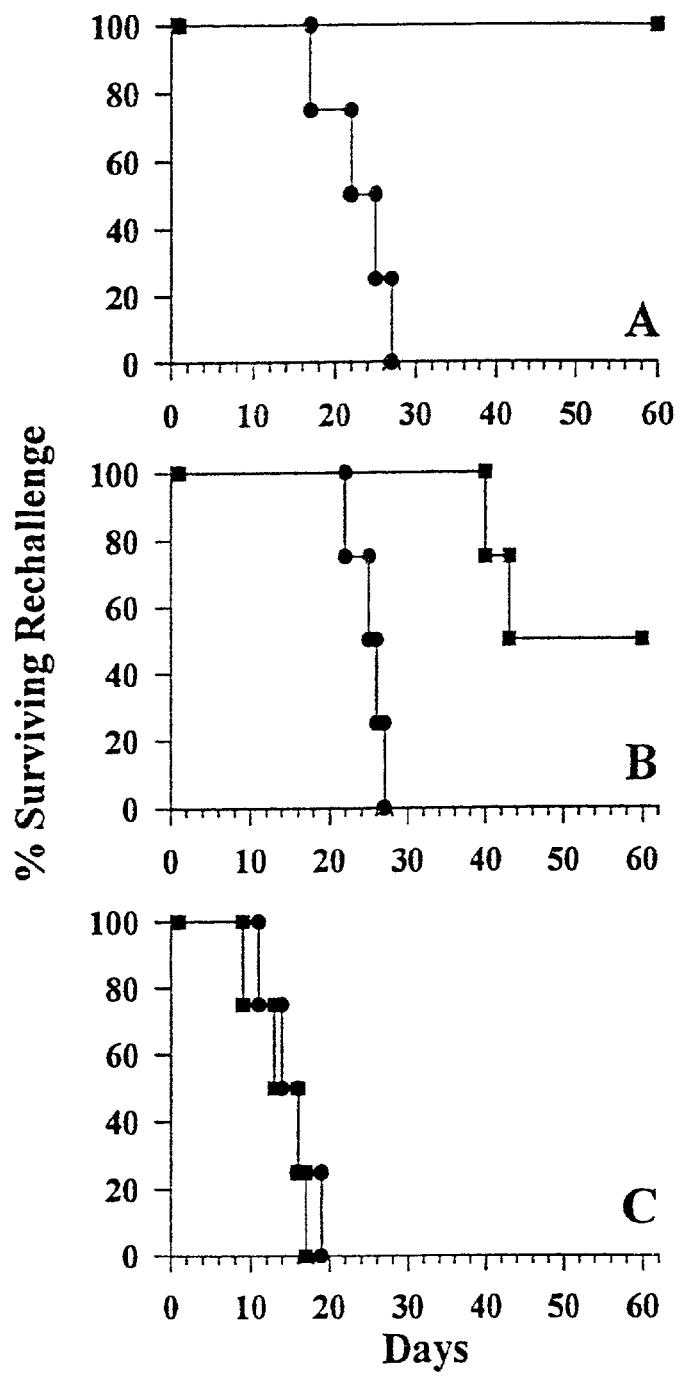
FIG. 6 is a graph showing that rats surviving intracranial implantation with live syngeneic glioblastoma cells expressing membrane M-CSF (■) but not naive controls (●) survive a subsequent intracranial challenge with parental glioblastoma cells (Panel A), or glioma cells (Panel B), but not adenocarcinoma cells (Panel C).

Animals that survived the i.c. challenges with T9/mM-CSF cells were subjected to i.c. rechallenges with $1 \times 10^5$ parental T9 glioma cells or $1 \times 10^6$ 9L glioma cells. The results (illustrated in FIG. 6) demonstrate that rejection of T9/mM-CSF cells is followed by a long-lasting glioma-associated immunity (■) compared with naive controls (●). These animals were 100% immune to i.c. challenges with parental T9 glioma cells (Panel A) and were partially protected from a challenge with 9L glioma cells (Panel B). In contrast, the animals were not protected from a challenge with $1 \times 10^5$ MADB106 mammary adenocarcinoma cells (Panel C).

Spleen cell transfer experiments were conducted to determine the origin of the acquired tumor-cell resistance. Results (illustrated in FIG. 7, Upper Panel) demonstrated that tumor resistance in the mM-CSF treated animals could be conferred by cells bearing the pan T-cell marker CD3. Transfer of spleen cells from T9/mM-CSF immunized animals into naive recipients resulted in immunity to i.c. challenge with $10^5$ T9 parental cells (●). However, transfer of immune spleen cells depleted of T cells by anti-CD3 plus complement did not confer tumor resistance (▼).

Tumor resistance could also be conferred by administering mM-CSF secreting cells at a site distant to the brain (FIG. 7, Lower Panel). $1 \times 10^7$ viable T9/mM-CSF cells injected s.c. in the flank were rejected in approximately one week. These animals were completely resistant to a subsequent i.c. challenge with parental T9 glioma cells (■). In contrast, animals initially treated with T9/LXSN vector control cells (●) were not resistant.

The combined results indicate that syngeneic mM-CSF expressing tumor cells initiate a systemic anti-tumor response that is reactive against tumor cells of the same tissue type. The tumor resistance is mediated, at least in part, by T lymphocytes.

Example 6

Secreted IL-4 Expression in a Syngeneic Vaccine Model

The use of an IL-4 producing cell line in a cancer vaccine was modeled in experiments using a Balb/c lymphoma line that secretes IL-4 at high concentration.

In one experiment, mice were coinjected with the lymphoma cells and the mouse melanoma cell line B16. Tumor growth was delayed by 2 weeks, in comparison with mice injected with B16 cells alone, or B16 cells mixed with non-cytokine secreting lymphoma cells. When the B16 cells were irradiated before mixing with the IL-4 cells, animals receiving the composition had no significant survival advantage against a subsequent challenge, compared with controls.

In another experiment, C57BL/6 mice were coinjected with IL-4 secreting lymphoma cells and the carcinoma cell line LL/2. Only one out of three mice developed tumor (the others were tumor-free), whereas all three mice in group injected with LL/2 alone developed tumor. Histologic examination of the one tumor in the treated group demonstrated prominent intratumor eosinophilia, as well as prominent splenic eosinophilia. The surviving mice are subsequently tested for immunity by rechallengwe with LL/2 cells alone.

Example 7

Use of Combination Vaccine Comprising Autologous Tumor Cells and IL-4 Secreting Allogeneic Cells in Human Ovarian Cancer This example describes a protocol for the use of a cellular vaccine in the treatment of human ovarian cancer. The vaccine comprises various amounts of IL4-secreting 4CI 107 cells (Example 1) mixed with autologous tumor cells.

Women diagnosed with Stage III or Stage IV epithelial ovarian cancer are candidates for this protocol. At the primary surgical staging laparotomy (day 0), a portion of tumor is collected, reduced to a single cell suspension, and used to establish both a primary cell culture and an autologous tumor master cell bank. Peripheral blood cells, and lymphocytes from the most cephalad para-aortic lymph node, are collected and frozen for future in vitro testing. Beginning on the fifth day, patients receive four weekly subcutaneous vaccine injections in the anterior thigh. Nine days after the last injection, patients begin weekly adjuvant chemotherapy, consisting of intravenous (i.v.) Cisplatin at 50 mg/m$^2$ for nine consecutive weeks.

A second set of four weekly mixed tumor cell vaccinations begins three weeks after the last course of chemotherapy. This set of vaccinations consists of the same concentration of cells as the first set. A second-look laparotomy is performed three weeks after the last vaccine injection. At this time, the surgeon performs an appropriate secondary debulking of any gross residual disease, and removes one or two pelvic, para-aortic or external iliac lymph nodes. The lymphocytes obtained from the draining nodes and the lymphocytes obtained at the end of the immunization procedures are compared with lymphocytes obtained at time 0 for in vitro analysis of the host's immunological response to autologous and allogeneic tumor cells as a result of receiving the vaccine. Skin testing is also conducted to evaluate the allogeneic and the autologous cell-mediated immune reactivity at various intervals during the protocol.

Subjects: Patients are eligible for this study if they fulfill all of the following criteria:

Women at least 18 years of age with histologically confirmed epithelial ovarian cancer: F.I.G.O. Stage III and Stage IV. A patient is considered a candidate for this protocol even with sub-optimally debulked disease. Primary staging laparotomy and other procedures are performed according to FIGO criteria (DiSaia et al. (1993) Clinical Gynecologic Oncology, St. Louis: Mosby—Year Book, pp 682-684).

Karnofsky Performance Status (DiSaia et al. supra p 375 ff) of at least 60 percent preoperatively and on the first day of treatment.

Clinically estimated life expectancy of at least three months.

Prior to receiving the first vaccination, patients must meet the following laboratory criteria: Hematocrit>20; Neutrophil count>1.5×10$^6$/ml; Platelet count>100,000; Creatinine<2.0.

Levels of CA-125 antigen must be>35 U/ml prior to surgery but not prior to the first vaccination.

Patients must provide sufficient tumor mass to generate all eight vaccine doses. The autologous tumor cells obtained at the time of debulking must be at least 80 percent viable and contain greater than 80 percent tumor cells.

Patients must be willing to participate in the study and provide informed consent.

Patients are ineligible for this study if they fulfill any of the following criteria:

Patients who have received any cytotoxic chemotherapy, radiotherapy or cytokine therapy within four weeks of entry.

Patients with known contraindication to platinum-based cytotoxic chemotherapy.

Patients with autoimmune diseases, lymphoproliferative diseases (including other hematologic malformative diseases), serological evidence of HIV exposure or any sign of active bacterial or viral infection or fever of unknown origin.

Patients with other concomitant invasive cancer.

Patients who within two months prior to entry were treated for a duration exceeding two weeks with immunosuppressive agents, including but not limited to corticosteroids and cyclosporine.

Patients who have received organ transplants, or who are pregnant or breast feeding.

Patients with psychological or geographic conditions which prevent adequate follow-up or compliance with the protocol.

Patients who are unable to provide informed consent.

Preparation of the Vaccine: The UCI-107 IL-4-E cell line (prepared as described in Example 1) has been extensively tested for the presence of microorganisms by our own and several independent outside laboratories. The following tests have been conducted by the following laboratories, and the results were all negative:

U.C.I. Laboratory: aerobic and anaerobic Bacteria.

Nichols Laboratory, San Juan Capistrano: mycoplasma pneumonial culture.

Quality Biotech, Inc., New Jersey: tested cells by DNA PCR for CMV, EBV, and HBV.

Co-cultivation of cells with Mus Dunni cells; amplification of cell supernatant with Mus Dunni cells for detection of replication competent retroviruses.

In addition, a mouse antibody production test for viruses is conducted as follows: PA317/LXSN IL-4 supernatant is injected intraperitoneally into mice. 0.7 to 1.0 ml of blood is drawn at four weeks after injection. The blood is sent to Dr. Dixie Fisher's laboratory, University of Southern California, Vivaria Animal Diagnostic and Research Laboratory, for serologic analysis for the following murine virus antibodies: ectromelia (integument); GD VII (central nervous system); Lactic dehydrogenase elevating virus (liver); Mouse hepatitis virus (digestive tract); Pneumonia virus of mice (respiratory tract); Reo-3 (intestinal tract); Sendai virus (respiratory tract). Cell supernatant is also tested for endotoxin and adventitious viral contaminants (Quality Biotech, Inc.).

Monolayers of UCI-107 IL-4-E cells for implantation are washed three times in PBS and established in Aim V medium. Aim V medium is approved for cell culture prior to implantation into patients and contains no bovine serum. Cells are passed in Aim V for two weeks before use in the vaccine preparations, then washed and resuspended in PBS. Cell viability is established by trypan blue exclusion. Cell suspensions with less than 90 percent viability are not employed.

Tumors are diagnosed by intraoperative examination of frozen sections. Once identified as an epithelial ovarian carcinoma, a portion of viable solid tumor tissue is aseptically collected, rapidly transported and processed within 4 hours into a single cell suspension by the method of Weisenthal et al.

One aliquot is used in an attempt to establish a primary cell culture. The remainder is resuspended in complete medium containing 10% DMSO, and aliquoted for storage under liquid nitrogen. The patient identification number and date of collection is recorded in a computer database and on each vial. The aliquoted frozen tumor cells are used as the autologous vaccine component. If a cell culture is established, it is used for in vitro testing; otherwise primary tumor cells are used. Tumor cells are manipulated and stored in AIM V medium plus 15 percent autologous human serum.

Both cells and medium from the autologous tumor master cell bank are tested for bacterial contamination at the time the vials are placed into the freezer. Samples are inoculated into thioglycolate medium for both aerobic and anaerobic bacteria; and streaked on trypticase soy yeast extract plates for aerobic bacteria. Cultures are incubated for five days at 37° C. Sample are also tested for endotoxins.

A 15 ml conical tube containing 10 ml CM and varying doses of UCI-107 IL-4-E and autologous tumor cells is irradiated for 50 minutes with a Cs137 source discharging 200 rads/min. After irradiation, th(vaccine cells are washed three times in normal saline and injected within 60 minutes.

Treatment Plan: Three patients are tested for each dose combination, unless the maximum tolerated combination, demonstrated by Grade III or greater toxicity or irreversible Grade II toxicity is observed. In this case, up to three additional patients are entered at the same dose level. If a second patient then develops the same degree of toxicity, that dose and cell combination is defined as the maximum tolerated combination. If none of the three additional patients develop the same degree of toxicity, the dose is escalated to the next level until the maximum level to be tested is reached. Intrapatient dose escalation is not performed.

The following table outlines the dosages used:

TABLE 8

| Number of autologous tumor cells | Number of UCI-107 IL-4-E cells | Ratio | Tumor mass required for full treatment schedule |
|---|---|---|---|
| $1 \times 10^7$ | $1 \times 10^8$ | 1:10 | 16-20 grams |
| $5 \times 10^7$ | $5 \times 10^7$ | 1:1 | 80-120 grams |
| $1 \times 10^8$ | $1 \times 10^7$ | 10:1 | 160-200 grams |

Inoculations are administered subcutaneously 10 cm inferior to the inguinal ligament on the anterior mid-thigh. The site of inoculation is alternated such that the first inoculation is administered to the left thigh, the next to the right thigh, and so on, using a 22 gauge needle.

The treatment schedule is as follows:

The date of cytoreductive surgery is marked as day 0.

Vaccine is given on days 5, 12, 19 and 26.

Adjuvant Chemotherapy: Nine days after the fourth vaccination, adjuvant chemotherapy consisting of i.v. Cisplatin at 50 mg/m$^2$×9 weekly cycles is administered (days 35, 42, 49, 56, 63, 70, 77, 84 and 91). Cisplatin, combination Cisplatin/Cyclophaphamide, or Cisplatin/Cyclophosphamide/Doxorobicin are believed to be approximately equivalent in terms of efficacy and toxicity, even when stratified for optimal versus suboptimal primary debulking. If deemed necessary, in addition to the Cisplatin, i.v. Taxol may be used as a salvage therapy.

Vaccine is given after the chemotherapy on days 112, 119, 126, and 133.

On day 154, patients undergo a second-look laparotomy that may include resection of residual tumor, removal of one or two palpably enlarged pelvic or para-aortic lymph nodes or inguinal lymph nodes, if necessary.

Patients are removed from the study under any of the following conditions:

Development of any Grade IV toxicity or Grade III toxicity related to administration of the vaccine. Grade II skin reactions are expected and not a grounds for removal from the study. Grade II reactions include localized rash, vaticoma, swelling, or a transient temperature of about 100.4° C.

Patient refusal to continue participation.

Disease Progression—Patients undergo a physical examination and determination of CA-125 levels prior to initiation of the chemotherapy and every three weeks thereafter. Disease progression is defined as a doubling of the CA->125. The post-surgical baseline sample is drawn with the first dose of chemotherapy and a doubling must have an absolute level of at least 70 U/ml and must be confirmed by repeat sample analysis.

Immunologic Testing: In vitro and in vivo immunological tests are conducted to determine if the immunization procedure has induced a host anti-tumor response. Baseline reactivity is established before the vaccinations begin. Reactivity against the allogeneic cell line serves as a positive control to measure patient reactivity against strong antigens.

The preparation of the specific lymphoid cell populations for immunologic testing is performed in the following manner. Peripheral blood mononuclear cells (PBMC) are collected from 50 cc of peripheral blood separated by FICOLL HYPAQUE™ gradients, and stored in liquid nitrogen.

Lymphocyte cytolytic activity and cytokine production is tested as follows: Cytolytic activity of the patient's lymphoid cells is measured in a 4 hour $^{51}$Cr release microplate assay and in long-term assays versus the allogeneic UCI-107 cell lines, autologous tumor cells, and another ovarian tumor cell line from a different patient as a specificity control.

Delayed Type Hypersensitivity (DTH) is tested by skin reaction. Test inoculations include: Mumps (viral), Trichophyton (fungal), PPD (bacterial) antigens, 5×10$^5$ irradiated autologous tumor cells, or 5×10$^5$ irradiated allogeneic tumor cells. Inoculums are administered into the forearm at separately marked sites. The diameter of induration is recorded 48 hours following inoculation, and skin test responses of less than 5 mm induration are scored as negative. DTH responses are assessed prior to vaccination (day 3), prior to chemotherapy (day 33), prior to the second series of vaccinations (day 111), and after the second series of vaccinations (day 152).

The ability of the vaccine combinations to improve the outlook of patients with ovarian cancer is also assessed according to standard clinical criteria.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed as the invention is:

1. A pharmaceutical composition formulated for human administration and effective in treating a neoplastic disease or eliciting an anti-tumor immunological response, comprising:
   a) a human cell expressing a cytokine from a recombinant polynucleotide; and
   b) a pharmaceutical excipient;
wherein the cytokine comprises a heterologous transmembrane region and is stably associated in the cell outer membrane, and
wherein the cell has been inactivated to prevent proliferation.

2. The method of claim 1, wherein the cytokine is selected from IL-4, IL-2, TNF-α, and M-CSF.

3. The composition of claim 1, wherein the cell is a cancer cell.

4. The composition of claim 1, wherein the cell is from a tumor of the same tissue type as a tumor in the human.

5. The composition of claim 1, wherein the cell is allogeneic to the human.

6. The composition of claim 1, wherein the cell is histocompatibly identical to the human.

7. The composition of claim 1, wherein the cell expressing the membrane-associated cytokine has been inactivated by irradiation.

8. The composition of claim 1, wherein the cell produces a secreted cytokine in addition to the cytokine stably associated in the outer membrane.

9. The composition of claim 1, wherein a majority of the cytokine produced by the cell is present on the outer membrane of the cell.

10. The composition of claim 1, wherein the cell has been transduced in vitro with a retroviral expression vector, or is the progeny of such a cell.

11. The composition of claim 1, wherein the cytokine is M-CSF.

12. The composition of claim 1, wherein the composition has been formulated for administration to an allogeneic human subject.

13. The composition of claim 12, wherein the cytokine is selected from IL-4, IL-2, TNF-α, and M-CSF.

14. The composition of claim 12, wherein the cell is a cancer cell.

15. The composition of claim 12, wherein the cell is from a tumor of the same tissue type as a tumor in the human.

16. The composition of claim 12, further comprising a tumor-associated antigen, wherein the combination of the cytokine and the tumor-associated antigen in the composition is effective in treating a neoplastic disease or eliciting an anti-tumor immunological response in the human.

17. The composition of claim 16, wherein the tumor-associated antigen is obtained from a cell autologous to the human.

18. The composition of claim 16, wherein the tumor-associated antigen is expressed by the same cells expressing the membrane-associated cytokine.

19. The composition of claim 16, comprising a combination of:

a) the cell expressing the membrane-associated cytokine; and
b) a tumor cell autologous to the human;
wherein the combination is effective in treating a neoplastic disease or eliciting an anti-tumor immunological response in the human.

20. The composition of claim 19, wherein the tumor cell is a primary tumor cell dispersed from a solid tumor obtained from the human.

21. The composition of claim 12, wherein the cell expressing the membrane-associated cytokine has been inactivated by irradiation.

22. The composition of claim 1, wherein the number of cells in the composition is at least about $5 \times 10^6$.

23. The composition of claim 1, with the proviso that said cytokine is not GM-CSF.

24. A pharmaceutical composition formulated for human administration and effective in treating a neoplastic disease or eliciting an anti-tumor immunological response, comprising:
a) a human tumor cell expressing a cytokine from a recombinant polynucleotide, wherein the tumor is ovarian cancer or brain cancer; and
b) a pharmaceutical excipient;
wherein the cytokine is stably associated in the cell outer membrane, and
wherein the cell has been inactivated to prevent proliferation.

25. A pharmaceutical composition formulated for human administration and effective in treating a neoplastic disease or eliciting an anti-tumor immunological response, comprising:
a) a human cell expressing a cytokine from a recombinant polynucleotide, wherein the cytokine is stably associated in the cell outer membrane, and the cell has been inactivated to prevent proliferation;
b) a pharmaceutical excipient; and
c) a tumor cell autologous to the human selected from a glioma, a glioblastoma, a gliosarcoma, an astrocytoma, and an ovarian cancer cell;
wherein the combination is effective in treating a neoplastic disease or eliciting an anti-tumor immunological response in the human.

26. The composition of claim 25, wherein the cytokine naturally occurs as a membrane cytokine.

27. A pharmaceutical composition formulated for human administration and effective in treating a neoplastic disease or eliciting an anti-tumor immunological response, comprising:
a) a human cell expressing an IL-4 from a recombinant polynucleotide; and
b) a pharmaceutical excipient;
wherein the IL-4 is stably associated in the cell outer membrane, and
wherein the cell has been inactivated to prevent proliferation.

28. The composition of any of claims 25 and 27, wherein the cytokine is a fusion protein comprising a heterologous transmembrane region.

29. A pharmaceutical composition formulated for human administration and effective in treating a neoplastic disease or eliciting an anti-tumor immunological response, comprising:
a) a human cell expressing a GM-CSF from a recombinant polynucleotide; and
b) a pharmaceutical excipient;
wherein the GM-CSF is stably associated in the cell outer membrane, and
wherein the cell has been inactivated to prevent proliferation.

30. A pharmaceutical composition formulated for human administration and effective in treating a neoplastic disease or eliciting an anti-tumor immunological response, comprising:
a) a human cell expressing a cytokine from a recombinant polynucleotide; and
b) a pharmaceutical excipient;
with the proviso that said cytokine is not M-CSF;
wherein the cytokine is stably associated in the cell outer membrane, and
wherein the cell has been inactivated to prevent proliferation.

31. The method of claim 30, wherein the cytokine is selected from IL-4, GM-CSF, IL-2, and TNF-α.

32. The composition of claim 30, wherein the cell is a cancer cell.

33. The composition of claim 30, wherein the cell is from a tumor of the same tissue type as a tumor in the human.

34. The composition of claim 30, wherein the cell expressing the membrane-associated cytokine has been inactivated by irradiation.

35. The composition of claim 30, wherein the cell produces a secreted cytokine in addition to the cytokine stably associated in the outer membrane.

36. The composition of any of claims 1, 27, 29, 23, and 30, further comprising a tumor-associated antigen, wherein the combination of the cytokine and the tumor-associated antigen in the composition is effective in treating a neoplastic disease or eliciting an anti-tumor immunological response in the human.

37. The composition of claim 36, wherein the tumor-associated antigen is obtained from a cell autologous to the human.

38. The composition of claim 36, wherein the tumor-associated antigen is expressed by the same cells expressing the membrane-associated cytokine.

39. The composition of claim 36, comprising a combination of:
a) the cell expressing the membrane-associated cytokine; and
b) a tumor cell autologous to the human;
wherein the combination is effective in treating a neoplastic disease or eliciting an anti-tumor immunological response in the human.

40. The composition of claim 39, wherein the tumor cell is a primary tumor cell dispersed from a solid tumor obtained from the human.

41. The composition of claim 39, wherein the tumor cell has been inactivated by irradiation.

42. The composition of claim 39, wherein the tumor cell has been inactivated by irradiation.

43. The method of claim 36, wherein the cytokine is selected from IL-4, IL-2, TNF-α, and M-CSF.

44. A unit dose of the composition according to claim 1, wherein the number of cells in the composition is at least about $5 \times 10^6$ but not more than about $2 \times 10^8$.

45. A method for producing the composition of claim 1, comprising transducing the cell in vitro with an expression vector encoding the membrane-associated cytokine.

46. The method of claim 45, wherein the expression vector is a retroviral vector.

47. The method of claim 45, wherein the cytokine is selected from IL-4, IL-2, TNF-α, and M-CSF.

48. The method of claim 45, wherein the cytokine is expressed under control of a cytomegalovirus (CMV) promoter.

49. The method of claim 45, wherein the cell is from a cancer of the same tissue type as a tumor in the human.

50. The method of claim 45, wherein the cell is allogeneic to the human.

51. The method of claim 45, wherein the cell is histocompatibly identical to the human.

52. The method of claim 45, further comprising inactivating the cell to prevent proliferation.

53. The method of claim 45, further comprising irradiating the cell.

54. A method for producing the composition of claim 36, comprising transducing a cell in vitro with an expression vector encoding the membrane-associated cytokine, and providing the transduced cell in combination with the tumor-associated antigen.

55. A method for producing the composition of claim 12, comprising transducing the cell in vitro with an expression vector encoding the membrane-associated cytokine.

56. The method of claim 55, wherein the expression vector is a retroviral vector.

57. The method of claim 55, further comprising inactivating the cell to prevent proliferation.

58. The method of claim 55, further comprising irradiating the cell.

* * * * *